United States Patent
Dourdeville et al.

(10) Patent No.: US 9,470,664 B2
(45) Date of Patent: Oct. 18, 2016

(54) CHROMATOGRAPHIC INTERFACE

(71) Applicant: Waters Technologies Corporation, Milford, MA (US)

(72) Inventors: Theodore A. Dourdeville, Providence, RI (US); Charles Phoebe, Uxbridge, MA (US); Rolf Grigat, Leverkusen (DE)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 609 days.

(21) Appl. No.: 13/939,731

(22) Filed: Jul. 11, 2013

(65) Prior Publication Data

US 2014/0014585 A1     Jan. 16, 2014

Related U.S. Application Data

(63) Continuation-in-part of application No. 13/252,684, filed on Oct. 4, 2011, now Pat. No. 9,024,635, which is a continuation of application No. PCT/US2010/031194, filed on Apr. 15, 2010, and a continuation-in-part of application No. PCT/US2010/030698, filed on Apr. 12, 2010.

(60) Provisional application No. 61/168,306, filed on Apr. 10, 2009.

(51) Int. Cl.
*G01V 3/00* (2006.01)
*G01N 30/04* (2006.01)
*G01R 33/30* (2006.01)
(Continued)

(52) U.S. Cl.
CPC .............. *G01N 30/04* (2013.01); *G01N 30/82* (2013.01); *G01R 33/307* (2013.01); *G01R 33/44* (2013.01); *G01N 24/08* (2013.01); *G01N 24/084* (2013.01); *G01N 24/085* (2013.01); *G01N 30/78* (2013.01); *G01N 2030/8411* (2013.01); *G01R 33/302* (2013.01); *G01R 33/46* (2013.01)

(58) Field of Classification Search
USPC ........................................................ 324/321
See application file for complete search history.

(56) References Cited

U.S. PATENT DOCUMENTS 4,086,051 A * 4/1978 Srinivas ............... B01D 53/025
                                                                   432/198
4,123,236 A    10/1978   Hirschfeld et al.
(Continued)

FOREIGN PATENT DOCUMENTS

GB          1524759 A     9/1978
JP          H11230957 A    8/1999

OTHER PUBLICATIONS

United Kingdom Combined Search and Examination Report under Sections 17 and 18(3) for Application No. GB1412171.9 dated Feb. 12, 2015.
(Continued)

*Primary Examiner* — Rodney Fuller
(74) *Attorney, Agent, or Firm* — McCarter & English, LLP; Deborah M. Vernon

(57) ABSTRACT

A chromatographic interface for sample handling and manipulation between separations or analyses is provided. The interface has an interfacing unit, a sample acquisition unit, and a sample trapping unit. The sample acquisition unit includes an inflow selector valve, an outflow selector valve, and one or more collection loops. The sample trapping unit includes a trap in fluid communication with the loop and having a stationary phase. The stationary phase can trap an analyte of interest from a fraction of the chromatographic sample separation flow. The tapping unit also has a scavenging gas source and a vacuum source; both can be used to substantially dry the stationary phase.

39 Claims, 17 Drawing Sheets

(51) Int. Cl.
  *G01R 33/44* (2006.01)
  *G01N 30/82* (2006.01)
  *G01N 24/08* (2006.01)
  *G01N 30/78* (2006.01)
  *G01N 30/84* (2006.01)
  *G01R 33/46* (2006.01)

(56) References Cited

U.S. PATENT DOCUMENTS

| | | |
|---|---|---|
| 4,281,246 A | 7/1981 | White et al. |
| 4,682,027 A | 7/1987 | Wells |
| 4,958,529 A | 9/1990 | Vestal |
| 5,847,564 A | 12/1998 | Smallcombe et al. |
| 5,938,932 A | 8/1999 | Connelly et al. |
| 6,152,989 A | 11/2000 | Ogawa et al. |
| 6,404,193 B1 | 6/2002 | Dourdeville |
| 6,456,078 B1 | 9/2002 | Iwata |
| 6,614,228 B2 | 9/2003 | Hofmann et al. |
| 6,641,783 B1 | 11/2003 | Pidgeon et al. |
| 6,790,361 B2 | 9/2004 | Wheat et al. |
| 8,115,930 B2 | 2/2012 | Anderson, Jr. et al. |
| 8,410,426 B2 | 4/2013 | Ozbal et al. |
| 8,414,774 B2 | 4/2013 | LaMarr et al. |
| 9,024,635 B2 | 5/2015 | Dourdeville et al. |
| 2002/0088946 A1 | 7/2002 | Hofmann et al. |
| 2007/0251824 A1* | 11/2007 | Patton ............. G01N 27/44782 204/461 |
| 2013/0265054 A1* | 10/2013 | Lowery, Jr. .......... G01R 33/281 324/319 |

OTHER PUBLICATIONS

Sturm et al., Liquid chromatography-nuclear magnetic resonance coupling as alternative to liquid chromatography-mass spectrometry hyperations: Curious option or powerful and complementary routine tool?, *Journal of Chromatography A,* 2012, 1259:50-61.

PCT International Search Report for Application No. PCT/US2020/030698, filed Apr. 12, 2010, form PCT/ISA/210, dated May 30, 2010.

PCT International Written Report for Application No. PCT/US2020/030698, filed Apr. 12, 2010, form PCT/ISA/237, dated May 30, 2010.

PCT International Search Report for Application No. PCT/US2020/031194, filed Apr. 15, 2010, form PCT/ISA/210, dated May 31, 2010.

PCT International Written Report for Application No. PCT/US2020/031194, filed Apr. 15, 2010, form PCT/ISA/237, dated May 31, 2010.

* cited by examiner

Shown during sample polishing phase of operation

Shown during back-elution phase of operation

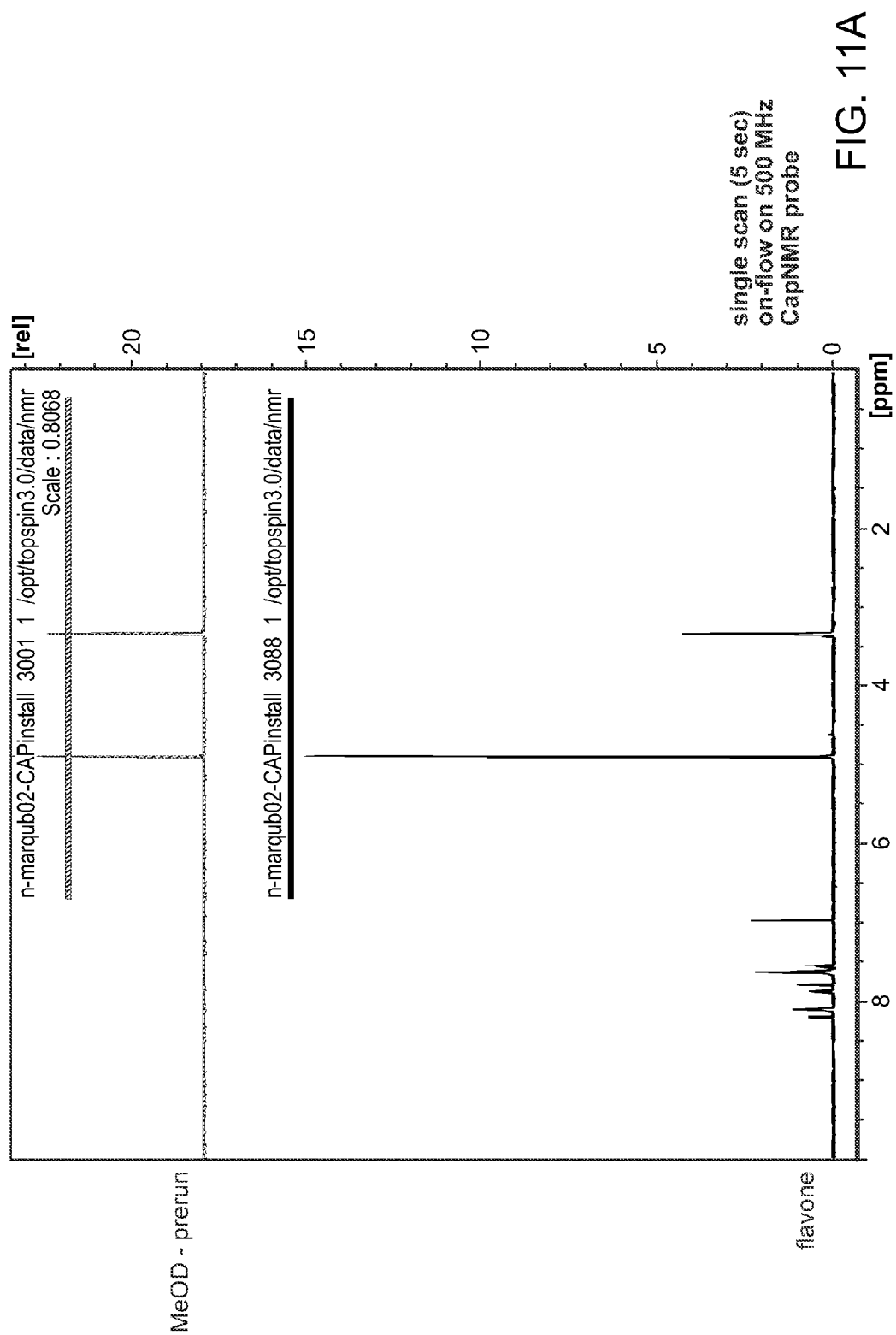

CHROMATOGRAPHIC INTERFACE

RELATED APPLICATIONS

This application is a continuation in part of U.S. application Ser. No. 13/252,684 filed on Oct. 4, 2011, which is a continuation of International Application No. PCT/US2010/031194 filed on Apr. 15, 2010 and a continuation in pan of International Application No. PCT/US2010/030698 filed on Apr. 12, 2010, winch claims benefit of a priority to U.S. Provisional Application No. 61/168,306 filed on Apr. 10, 2009. The contents of all these applications are incorporated herein by reference in their entirety.

FIELD OF THE INVENTION

The invention, in various aspects and embodiments, relates generally to apparatuses and methods for chromatographic interfacing (e.g., sample handling and manipulation between separations or analyses). More particularly, the invention relates to apparatuses and methods for selectively collecting and/or preparing one or more analytes in a sample, and interfacing between essentially any type of liquid/fluid/condensed phase chromatography and essentially any type of spectroscopic, separation, or analytical method.

BACKGROUND OF THE INVENTION

The increasingly widespread use of complex samples and advanced spectroscopic detectors such as mass spectrometers has dramatically broadened the utility and information yield of analytical chromatographic separations. Earlier detection techniques such as refractometry or fixed wavelength ultraviolet absorbance detection might imply the presence of a suitable analyte within the detection volume, and with the use of known calibrators, might imply the concentration of the analyte. However, the identity of the analyte, at best, was inferred by comparison with the chromatographic retention time or retention volume of a known standard. Identification of the analyte was effectively not a property or a capability of such detection subsystems.

Such detectors were also susceptible to significant quantitation errors in the presence of overlapping chromatographic bands or zones, limiting their utility in the analysis of highly complex mixtures as are commonly encountered in biological and environmental applications. Historically, the application of mass spectrometry to chromatographic detection facilitated analyte detection within vastly more complex mixtures, by permitting high resolution separation in the mass-to-charge domain to augment chromatographic separation in the fluid volume domain.

Depending upon the mode of mass spectrometric analysis being performed, and the nature of the analyte(s), putative compound identification might be performed in line during the separation, substantially without reliance upon the chromatographic retention time or retention volume of a standard. There exist, however, important classes of compounds for which mass spectrometry alone is not capable of rendering a full and complete identification. Commonly, examples are found where isomerization is present, where the isomers share or exhibit the same chemical formula and parent mass to charge ratio, but are assembled in arrangements which can be either structurally or spatially distinct. Knowledge of the chemical formula, while useful, is incomplete if the configuration or arrangement of the molecule is questionable or fully unknown. Isomers can have distinctly (in some cases, radically) different behaviors within biological systems, if supplied as pharmaceutical compounds, or if rendered as degradation products.

SUMMARY OF THE INVENTION

The present invention provides for interfacing between the separation (e.g., liquid chromatography "LC," supercritical fluid chromatography "SFC," or other fluid chromatography methods) of a sample and the analysis or study of the sample (e.g., by nuclear magnetic resonance spectroscopy "NMR," mass spectrometry "MS," porous complex Single-Crystal [X-Ray] Diffraction "SCD" or other assay such as a chemical assay or bioassay). This coupling can be a fundamentally important component in the toolkit of those working, for example, in pharmaceutical, environmental, homeland security, natural products, food/agriculture, or forensic fields. In various aspects and embodiments, the present invention provides for the separation, handling, and focusing one or more analytes while interfacing between the chromatographic separation and analysis of a sample. In NMR-based applications, the present invention further provides for the elimination of interference from protonated solvent(s).

In one aspect, the invention features, an apparatus for chromatographic interfacing including an interfacing unit, a sample acquisition unit, and a sample trapping unit. The interfacing unit includes (i) a chromatographic inflow valve adapted to receive a chromatographic sample separation flow, (ii) a chromatographic outflow valve adapted to allow discharge of the sample separation flow, (iii) a loop expulsion inflow valve adapted to receive an expulsion fluid flow, and (iv) a loop expulsion outflow valve in fluid communication with the loop expulsion inflow valve and adapted to allow discharge of a field. The sample acquisition unit includes (i) an inflow selector in selectable fluid communication with the chromatographic inflow valve or the loop expulsion inlet valve, (ii) an outflow selector in fluid communication with the loop expulsion outflow valve, and (iii) one or more collection loops, each loop being independently selectable so establish fluid communication between the inflow selector valve and the outflow selector valve. The sample trapping unit includes (i) a trap in selectable fluid communication with the loop expulsion outflow valve and defining a flow path from a first port to a second port and through a stationary phase disposed therebetween, the stationary phase adapted to trap an analyte of interest from a fraction of the chromatographic sample separation flow, and (ii) a scavenging gas source in selectable fluid communication with the flow path and a vacuum source in selectable fluid communication with the flow path, the scavenging gas source and vacuum source adapted to substantially dry the stationary phase.

In another aspect, the invention features, a method of chromatographic interfacing. The method includes the steps of trapping an analyte from a chromatographically separated traction of a sample onto a stationary phase disposed within a trap defining a flow path through the first port to a second port and a stationary phase disposed therebetween; and flowing a scavenging gas, into a first port of the trap and concurrently achieving a vacuum at the second port, through the flow path, thereby drying the stationary phase.

In yet another aspect, the invention features a method of chromatographic interfacing. The method includes the steps of: (i) chromatographically separating a first fraction comprising a first analyte from a sample; (ii) accumulating the first fraction in a sample collection loop; (iii) trapping the first analyte on a stationary phase disposed within a trap defining a flow path through a first port to a second port and the stationary phase disposed therebetween; (iv) flowing a scavenging gas, into the first port of the trap and concurrently achieving a vacuum at the second port, through the flow path, thereby drying the stationary phase; and (v) eluting the first analyte.

In different embodiments, any of the aspects above can be combined with any one or more of the features below.

In some embodiments, the apparatus includes or the method employs a sample acquisition unit that further includes one or more bypass loops, each bypass loop being independently selectable to establish fluid communication between the inflow selector valve and the outflow selector valve.

In some embodiments, the apparatus includes or the method employs a sample acquisition unit that further includes two or more collection loops and two or more bypass loops, each loop being independently selectable to establish fluid communication between the inflow selector valve and the outflow selector valve.

In some embodiments, the apparatus includes or the method employs a chromatograph providing the flow from the chromatographic separation of the sample. The chromatograph can be a liquid chromatograph or a supercritical fluid chromatography.

In some embodiments, the apparatus includes or the method employs an inflow selector that comprises a low-internal-volume rotary shear-seal valve herein termed a slice valve.

In some embodiments, the apparatus includes or the method employs an inflow selector and outflow selector that comprise a rotary selector valve for establishing fluid communication between a predetermined collection loop or bypass loop. The rotary selector valve can comprise a break-before-make design.

In some embodiments, drying the stationary phase comprises eliminating substantially all solvent. The solvent can comprise a protonated or deuterated solvent.

In some embodiments, the scavenging gas comprises dry N2 gas. The scavenging gas can consist of, or consist essentially of dry N2 gas. Dry nitrogen can be provided from a cryogenic system.

In some embodiments, the apparatus includes or the method employs a scavenging gas source that is adapted to provide a pulsed introduction of compressed N2 gas.

In some embodiments, the apparatus includes or the method employs a scavenging gas source that further comprises a restrictor (e.g., capillary restrictor) adapted to control pressure at the first port and/or the second port of the trapping column, flowing the scavenging gas can comprise restricting the flow of the scavenging gas.

In some embodiments, the apparatus includes or the method employs a vacuum source that comprises a dry pump, or an oil sealed pump having an inline filter adapted to remove volatilized oil backstreaming from the oil sealed pump.

In some embodiments, the apparatus includes or the method employs a vacuum source controller adapted to determine when the trap is dry.

In some embodiments, the apparatus includes or the method employs an analyte detector and a controller adapted to determine when the analyte of interest, is present in the chromatographic stream and to control the Inlet selector accordingly.

In some embodiments, the apparatus includes or the method employs an eluting solvent source.

In some embodiments, the apparatus includes or the method employs a spectrometer for analyzing the analyte of interest.

In some embodiments, the apparatus includes or the method employs a chemical or bioassay for analyzing the analyte of interest.

In some embodiments, the apparatus includes or the method employs, a time delay controller adapted to adjust for dead volume.

In some embodiments, the method includes or the apparatus is adapted for flowing the scavenging gas using a pulsatile introduction of scavenging gas. Pulsatile introduction of scavenging gas can comprise providing 'ON' pulses of about 100-200 milliseconds duration at a duty cycle of 1% or less.

In some embodiments, the method includes or the apparatus is adapted for flowing the scavenging gas at a rate of about 0.0001 to 0.01 SCCM.

In some embodiments, the method includes or the apparatus is adapted for drying the stationary phase by achieving a vacuum having a pressure of less than about 15 mTorr. Drying the stationary phase can comprise eliminating substantially all solvent. Drying the stationary phase can comprise substantially achieving the base pressure of the vacuum source.

In some embodiments, the method includes or the apparatus is adapted for flowing a weak solvent comprising at least one of a protonated or deuterated solvent through the flow path during trapping.

In some embodiments, the method includes or the apparatus is adapted for eluting the analyte using DMSO-d6.

In some embodiments, the method includes or the apparatus is adapted for, separating the at least one traction and trapping the analyte further by the steps of: (1) detecting the presence of the analyte during primary chromatographic separation; (2) flowing the at least one traction through a slice valve to a selector valve; (3) switching the selector valve from a bypass loop position to a collection loop position; (4) detecting at least one of the absence of the analyte and the presence of an undesired contaminant; and (5) switching the selector valve from the collection loop position to the bypass loop position.

In some embodiments, the method includes or the apparatus is adapted for (i) chromatographically separating a second fraction comprising a second analyte from the sample; (ii) accumulating the second fraction in a second sample collection loop; (iii) trapping the second analyte on the stationary phase of the trap after eluting the first analyte; (iv) flowing the scavenging gas, into the first port of the trap and concurrently achieving a vacuum at the second port, through the How path, thereby drying the stationary phase; and (v) eluting the second analyte.

In some embodiments, the method includes or the apparatus is adapted for trapping the first analyte on the stationary phase disposed within a trap comprises flowing the first fraction from the first port to the second port and eluting the first analyte comprises flowing an eluting solvent from the second port to the first port; or trapping the first analyte on the stationary phase disposed within a trap comprises flowing the first fraction from the second port to the first port and eluting the first analyte comprises flowing an eluting solvent from the first port to the second port.

An embodiment of the present invention is directed to a device for performing a chromatographic separation and a nuclear magnetic resonance (NMR) analysis on a sample. The device comprises an interfacing unit, sample acquisition unit, and sample trapping unit as discussed above, the sample acquisition unit receiving a flow from a chromatograph assembly and the trapping unit being providing a flow to an NMR assembly. Other embodiments can employ any one or more spectroscopic or analytical techniques (e.g., as discussed herein) in place of an NMR assembly. The device can further include a controller in signal communication with the chromatographic assembly and the nuclear magnetic resonance assembly, to receive retention time data and nuclear magnetic resonance data and associating the retention time data and nuclear magnetic resonance data to at least one fraction of the sample separation flow.

Chromatographic assemblies can include equipment and ancillary devices for performing chromatographic separations. As used herein, the term chromatographic device can refer to a column, cartridge, capillary, and/or other inline plumbed separation device. Such separation devices are typically packed with particles, beads, porous monolith and the like, although capillary type devices can rely on internal wall structures. Thus, the chromatographic assembly performs separations under pressure. In the manner of high pressure liquid chromatography (e.g., up to 6,000 PSIG head-pressure), and even higher pressure liquid chromatography, ultra high performance chromatography (e.g., up to 15,000 or 20,000 PSIG head-pressure), and supercritical land chromatography (e.g., up to 10,000 PSIG).

Controller can include a computer or CPU and supporting software, firmware, and instructions. The computer or CPU can be a personal computer, mainframe, server or integral with one or more assemblies of the device. The term signal or signal communication can be used in an optical, electrical, magnetic or mechanical sense to denote wired, radio or photo communication and signaling.

NMR assemblies can be used to refer to equipment and ancillary devices for performing nuclear magnetic resonance analysis. The NMR, or other analytical/spectroscopic, assembly is in fluid communication with a trap and can receive a sample for analysis through elution of an analyte from the stationary phase within the trap. In this context, the trap has the advantage of focusing and/or concentrating the analyte. In the example of NMR, the trap has the advantage of mitigating interference from protonated solvents, through the drying of the stationary phase within the trap.

Flows (e.g., liquid and/or condensed phase flows, as well as combinations thereof) can be transmitted through conduits such as tubing, piping, conduits, capillaries and ail associated fittings, valves, and ancillary supporting components and the like for placing components and assemblies in fluid communication. As used herein, the term fluid communication can mean plumbed together, as in linked by conduits, to move fluids therebetween.

In some embodiments, the method includes using or the apparatus further comprises a peak detector. The peak detector can be in fluid communication with the conduit and is lit signal communication with the controller. The peak detector can produce one or more signals corresponding with an analyte of interest or a potential analyte of interest in a separated sample to isolate the separation sample to form an isolated separated sample. The peak detector can direct the isolated separated sample to at least one of the nuclear magnetic resonance and the second detector.

In some embodiments, the method includes using or the apparatus further comprises a valve in fluid communication with the conduit to facilitate the directing of the isolated separated sample. One example valve is adapted for receiving the isolated separated sample and forming isolated separated sample aliquots and directing at least one isolated separated sample aliquots to the nuclear magnetic resonance and the second detector such that said isolated separated sample aliquot is associated by controller with nuclear magnetic resonance data, the second detector data and retention time data. As used herein, valve can refer to one or more valves used singularly, or in groups.

In various embodiments, the present invention facilitates structure elucidation of small molecules. For example, embodiments featuring a nuclear magnetic resonance assembly having relatively simple ID proton NMR mode, and a relatively simple spectrometer of modest size (at-bench magnetic resonance detector or "MRD", if sufficient sample (and sample concentration) is available, can be employed to carry out the NMR portion of the analysis. In small molecule analysis, it is the coupling of mass spectrometry and NMR spectroscopic techniques which effectively underpins and enables structure elucidation. The rules of such elucidation, at least for small molecules, are sufficiently well known that commercial software packages have been written to accomplish this in a substantially automated manner (see, e.g., http://www.acdlabs.com/products/spec_lab/complex_tasks/str_elucidator/, Advanced Chemistry Development Inc., Toronto, Ontario, Canada M5C IT4).

Offline NMR spectroscopy of properly prepared samples resident in vials (e.g., NMR tubes) is an established technique within dedicated NMR laboratories. The coupling of NMR spectroscopy with liquid chromatography introduces a different set of problems than those encountered in the coupling of mass spectrometry with liquid chromatography. Mass spectrometric analysis typically has the sensitivity taxi speed to interface directly in real time with a liquid chromatography separation (whether high performance liquid chromatography (HPLC), or ultra high performance liquid chromatography ("UHPLC"). NMR spectrometers make use of weaker signals, and typically require both a larger sample mass (and sample concentration) to be present for analysis, and typically require a longer sample interrogation time than can be accommodated by the chromatography. Moreover, achievement of a usefully large signal to noise ("S/N") ratio in the proton NMR of dissolved species can require the substitution of a deuterated solvating phase for the normally non-deuterated solvating phase in which the sample is typically chromatographed (e.g., $D_2O$ is substituted for $H_2O$, $CD_3CN$ is substituted for $CH_3CN$, DMSO-d6 is substituted for DMSO (dimethyl sulfoxide)), reduction of the solvent background signal being the intent of deuterated solvent substitution. The present invention provides alternative apparatus and methods for mitigating protonated solvent interference, through the removal (rather than mere substitution) of protonated solvent.

Embodiments of the present invention can feature conventional scale LC accomplished with columns of typically 2.1 mm internal diameter, and chromatographic pressures which can be greater than 5,000 PSIG, or a supercritical fluid chromatography (SFC) separation technique, coupled with an NMR spectroscopic technique. Embodiments of the present invention feature a primary chromatographic separation of a peak of Interest corresponding to a potential analyte of interest, and the temporary isolation and accumulation of that analyte of interest within a fluid conduit offline from the separation stream, or accumulating from a single or from a plurality of LC runs, the transfer of the analyte of interest from that fluid conduit to a trapping column containing a stationary phase on which the analyte can be retained and focused, purge out of protonated solvent from the trapping column, trapping valve, and associated tubing by a dry scavenging gas (e.g., dry N2). When removal of protonated (and, potentially, deuterated) solvent from the trap is substantially complete, step-elution of the analyte from the trapping column is accomplished by a second deuterated phase (optionally deuterated DMSO (DMSO-d6) or deuterated acetonitrile ($CD_3CN$) in the case of a reversed phase LC trapping mode), where the analyte is thereby conveyed downstream to an NMR spectrometer flow probe as a highly concentrated step-elution band, and parking of that focused band within the interrogation region of the detector cell of the flow probe of the NMR spectrometer, until NMR spectroscopy is complete. Upon completion of NMR spectroscopy, the analyte is unparked or migrated out of the How probe, typically to a waste receptacle, although other routes of emergence from the flow probe can be readily contemplated if the analyte is to be further used.

In the context of the above description, it can be helpful to introduce the concept of impedance matching between the LC separation and the detector cell of the NMR probe. To achieve a suitably high degree of sensitivity in the NMR analysis (e.g., to be able to carry out the NMR analysis with a suitably small mass of analyte material) it can be advantageous to make use of a microcoil NMR probe configuration. Such probes are commercially available through Magnetic Resonance Microscissors (MRM) Corporation (Savoy, Ill., USA), a division of Protasis Corporation (Marlborough, Mass., USA). Microcoil probes achieve high S/N with relatively low sample mass requirements through the use of a very small detection cell volume (typically 2.5 or 5.0 microliter interrogated volume) which is encompassed within a correspondingly small excitation and detection radiofrequency (RF) coil. To make appropriate use of such a cell, the chromatography zone or band conveying the dissolved analyte must be of a few microliter volume and the analyte must be present at sufficiently high, concentration that an appropriate number of analyte molecules are present within that few microliter volume. Typically, analyte concentrations at the milliMolar (mM) level (1 to 30 mM typically) are required, depending upon the nature of the NMR spectroscopy being performed, 1 to 30 mM analyte concentrations are higher than what is typically manipulated within analytical LC separations and zones or bands of few microliter volume are smaller than what is typically manipulated in conventional analytical LC separations.

In this context, impedance matching is an electrical design practice wherein properties of an electrical load and an electrical source are matched so as to maximize the power transfer between the two, and minimize reflections from the load. Impedance matching is a useful concept which is discussed in contexts other than electrical design. Examples include acoustic impedance matching, optical impedance matching, and mechanical impedance matching. In the coupling of LC with microcoil NMR spectroscopy, one is confronted with a situation where analyte in the LC process resides at lower concentration and at larger volume than is useful for insertion into a microcoil probe. The microcoil probe requires relatively intense analyte concentrations to exist in relatively minute volumes. In common between the two is the presence of a total analyte mass, which one would like to convey from one process (LC) to a second process (NMR) with high efficiency and with little or no loss or wastage. We introduce here the concept of impedance matching between, e.g., a 2.1 mm internal diameter column LC separation, and a microcoil probe. Such impedance matching makes use of chromatographic principles, and incorporates at least one additional column device containing a retentive phase, beyond the primary separation column. In usage sequences detailed below, this additional column device is selected to be highly retentive for the classes of analyte of interest, and to have a relatively small bed volume. The purpose of this column device, which can be referred to as a trap or trapping column, is to process a relatively dilute incoming sample fractionated or sliced from a primary chromatography separation, where such processing results in the analyte becoming immobilized (and thus distributed over) a retentive bed of relatively small volume. Once immobilized there, the analyte can be washed of salts or other mobile phase modifiers which might be present in the primary chromatography separation, and which can disrupt or degrade the quality of the NMR spectroscopy. Protonated solvent can also be substantially eliminated while the analyte of interest is retained on the trap bed. Washing steps can optionally make use of inert gas purges between liquid phase introduction steps. When washing of the retained analyte is complete, a final men gas purge step is undertaken, followed by assertion of gas and vacuum on the trap bed, prior to analyte elution. In a preferred embodiment, the trap is packed with the stationary phase OASIS™ HLB (Waters Technologies Corporation, Milford, Mass., USA), and the elation solvent is DMSO-d6. Following the final gas and vacuum purge step, the elution solvent arrives in a sharp front, and conveys the analyte downstream in a densely concentrated band. The analyte concentration and volume within this new hand are now appropriate for matching with the properties of the microcoil probe. This low volume, high concentration eluted band is conveyed to the microcoil NMR probe and parked there for the duration of the NMR analysis. Absent this impedance matching function, the analyte as eluted from the primary chromatography separation would be poorly and inadequately utilized by a microcoil NMR probe, and little overall analytical utility would be achieved.

While a reversed phase mode of analyte trapping is described above, operating in conjunction with a reversed phase mode of chromatographic separation in the primary chromatography system, it is readily envisioned that other trapping modes can be employed, such as normal phase trapping, or the use of specialized stationary phases and separation techniques as appropriate to the separation of chiral compounds.

Sample trapping on a sorbent can focus the peak and effect the substantial elimination of protonated solvents. With trapping in accordance with the present invention, there is no requirement to manually dry the sample in a vial and resolvate it in a new (deuterated) solvent system. The trapping asset and related system control enable full system automation, where a ran can be properly configured, and a structure elucidated as a result (e.g., the analyst can configure an analysis, and return to be presented with an elucidated structure from this automated system, not just a chromatogram or other lower level ensemble of data).

One example trapping sorbent is packed in a column housing which is non-ferromagnetic, and connected to the chromatography system using tubing which is similarly non-ferromagnetic, such that the trap can be positioned very close to the flow probe entry point. Thus the distance intervening between the NMR spectrometer and the primary chromatography system can be bridged by a solvent flow where, by design, analyte is refocused proximal to the entrance to the NMR flow probe. Substantial elimination of the zone broadening associated with analyte transport to the NMR spectrometer is an enabling capability to ensure that analyte concentration within the NMR detector cell is maximized. Analogous advantages exist for other spectroscopic and analytical apparatus and methods.

Elution of analyte on a relatively sharp step-gradient front can present a solvent susceptibility mismatch when NMR probe shimming is underway. This matter is discussed in some detail in U.S. Pat. No. 6,404,193, which is of common inventorship with the present disclosure, and which is incorporated herein by reference. The fluid path residing between the trap column and the outlet of the NMR detector cell can, under automated system control, be prefilled with the strong (e.g., organic) deuterated solvent which is subsequently used to elute the analyte from the trap. Only after this pre-filling is accomplished, is the trap valve switched such that the deuterated organic flow can elute the analyte from the trap. The pre-filling of the fluid path downstream of the trap column is intended to substantially reduce the magnitude of the solvent discontinuity which exists at or near the NMR detector cell at the time of detection, thereby reducing or partially mitigating spectral line broadening associated with susceptibility mismatch.

These and other features and advantages of the present invention will be apparent to those skilled in the art upon reading the detailed description that follow and viewing the Drawings.

DETAILED DESCRIPTION OF THE INVENTION

Figure 1:
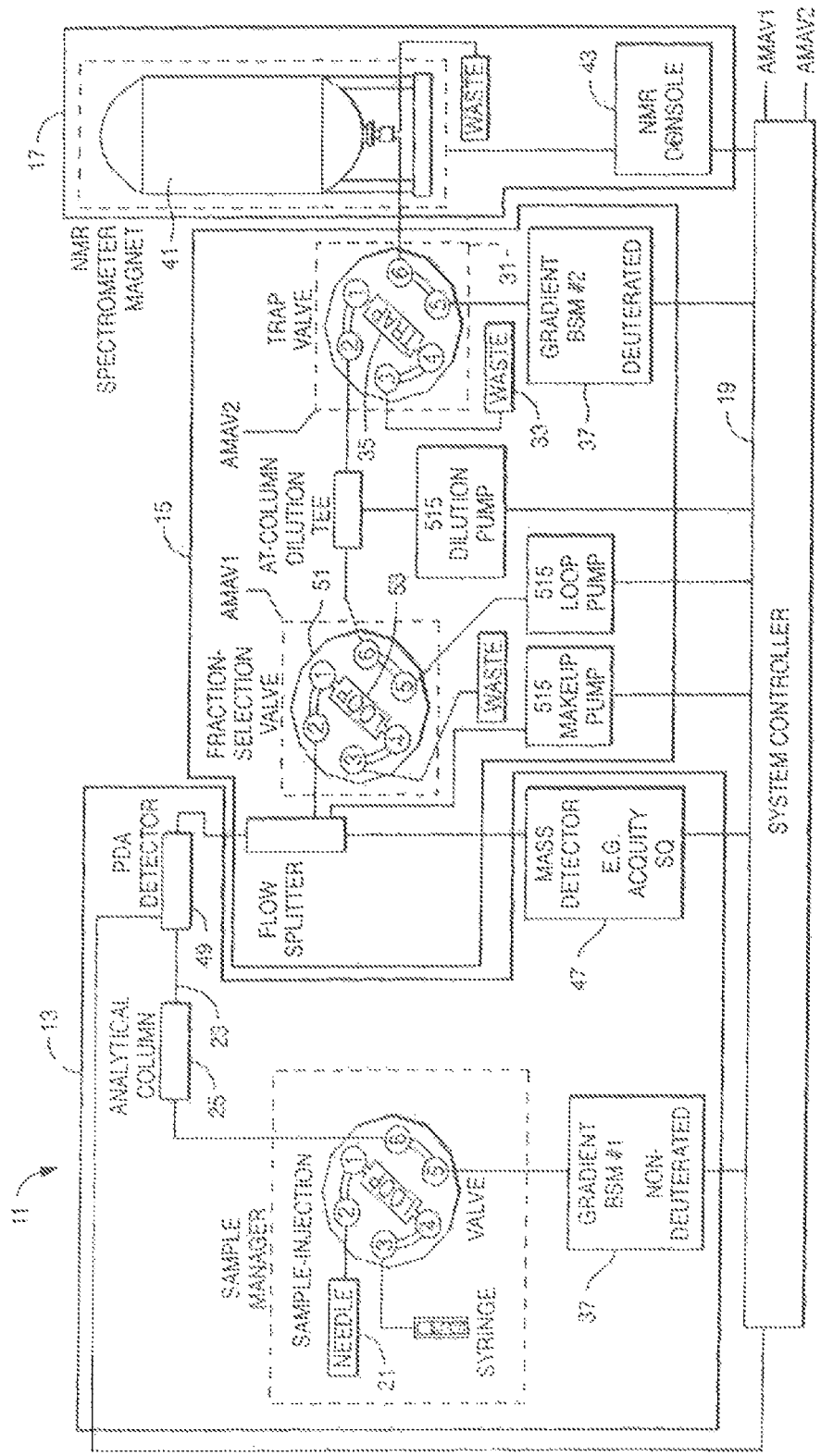
FIG. 1 depicts, in schematic form, one example device incorporating features of the present invention.

The present invention provides for interfacing between the separation (e.g., liquid chromatography "LC" supercritical fluid chromatography "SFC," or any other fluid chromatography) of a sample and the analysis or study of the sample (e.g., by NMR, MS, SCD, or other assay such as a chemical assay or bioassay). In various aspects and embodiments, the present invention advantageously provides for the separation, handling, and focusing one or more analytes while interfacing between the chromatographic separation and analysis of a sample. In NMR based application, the present invention further provides for the advantageous elimination of interference from protonated solvent(s).

With respect to apparatuses, the present invention provides for specialized chromatographic interfacing equipment. Apparatuses can include a sample acquisition unit (e.g., having an inflow selector, and outflow selector, one or more collection loops) and a specialized trapping unit (e.g., having a trap in fluid communication with the sample acquisition unit and a scavenging gas source for dying the stationary phase of the trap). The sample acquisition turn and trapping unit can further include, or operate in the context of, an interfacing unit (e.g., for receiving a chromatographic outflow and providing a sample to an analytical instrument; as well and separation-analysis systems (e.g., LC-MS or LC-NMR). This specialized equipment is discussed, for example, in terms of structure in connection with FIGS. 6A-D. Furthermore, examples of separation-analysis systems in which the present invention can operate are discussed in connection with FIGS. 1-4.

With respect to methodology, the present invention provides for specialized chromatographic interfacing methods, for example, methods can includes the steps of (i) trapping an analyte from a chromatographically separated fraction of a sample onto a stationary phase disposed within a trap defining a flow path through the first port to a second port and a stationary phase disposed therebetween and (ii) flowing a scavenging gas, into a first port of the trap and concurrently achieving a vacuum at the second port, through the flow path, thereby drying the stationary phase.

Similarly, chromatographic interfacing methods can include the steps of (i) chromatographically separating a first fraction comprising a first analyte from a sample; (ii) accumulating the first fraction in a sample collection loop; (iii) trapping the first analyte on a stationary phase disposed within a trap defining a flow path through a first port to a second port and the stationary phase disposed therebetween; (iv) flowing a scavenging gas, into the first port of the trap and concurrently achieving a vacuum at the second port, through the flow path, thereby drying the stationary phase; and (v) eluting the first analyte.

Examples of such chromatographic interfacing methodologies are discussed, for example, in FIGS. 7-D and 8. Furthermore, examples of advantages achieved through implementation of the present invention are discussed in connection with FIGS. 9A, 9A, 10, 11A, and 11B.

The detailed description of various aspect and embodiments of the present invention is continued below. The description begins with a discussion of interfacing in separation-analysis systems (e.g., LC-MS or LC-NMR), including examples of various structures and workflows that can be involved. Next, the detailed description discusses, in further detail, the slicing of multiple peaks from a chromatogram. Then, the detailed description discusses, in further detail, principles of analyte trapping and polishing (including data illustrating advantages of the present invention).

After addressing interfacing separation-analysis systems, as well as slicing, trapping, and polishing analyses, the detailed description discusses aspects of generalizing the interfacing techniques (e.g., beyond NMR, applications). Next, the detailed description discusses, in further detail, the mitigation of protonated and/or deuterated solvent interference. Then, the detailed description discusses, in further detail, drying as an alternative to liquid phase equilibration processes for elimination of protonated solvents (including data illustrating advantages of the present invention) and the use of DMSO-d6 as an elution solvent in accordance with the present invention. Finally, the detailed description discusses and application of the present invention to LC-SCD (X-Ray Single Crystal Diffraction).

Interfacing in Separation-Analysis Systems (e.g., LC_NMR)

FIG. 1 illustrates one embodiment of the present invention, directed to a device for performing a chromatographic separation and a nuclear magnetic resonance analysis on a sample, generally designated by the numeral 11. The device 11 comprises a closed chromatographic assembly 13, conduit 15, NMR assembly 17 and controller (in the form of system controller) 19. In various embodiments, the invention advantageously asserts a vacuum along with a restricted delivery of dry gas, to scavenge a trap bed.

Turning first to the chromatographic assembly 13, the chromatographic assembly is closed in the sense that the chromatography is performed in a vessel of pipe closed and contained from the atmosphere. The chromatographic assembly 13 has an input in the form of a needle 21, an outlet 23, one or more pumps 37 and a chromatographic device 27.

The input 21 can receive one or more samples. The output 23 can discharge one or more separated samples. The chromatographic device 25 includes a column, cartridge, capillary or other inline plumbed separation device. Such separation devices are typically packed with particles, beads, porous monolith and the like, although capillary type devices can rely on internal wall structures. The chromatographic device 25 can separate the sample to form one or more separated samples having retention time data.

Conduit 15 is in fluid communication with the outlet 23 of the closed chromatographic assembly 13 for conveying the one or more separated samples to the nuclear magnetic resonance assembly 17. Conduit 15 encompasses tubing, piping, conduits, capillaries and all associated fittings, valves, and ancillary supporting components and the like for placing components and assemblies in fluid communication. As used herein, the term "fluid communication" means plumbed together, as in linked by pipes, tubing and the like, to move fluids therebetween.

As depicted, conduit 15 includes a trap 31 for holding a separated sample to form a held separated sample and placing said held separated sample in said nuclear magnetic resonance assembly 17. The trap 31 forms a held separated sample and a passed separated sample. A passed separated sample can be discharged from the device at trap waste 33. An example trap includes a trapping column 35 or a separated sample loop [not shown] or a vessel [not shown]. The trapping column 35 is plumbed to a trap 31 allowing unwanted fluids to be discharged and desired deuterated reagents to elute analytes. In this example, trap 31 is in fluid communication with nuclear magnetic resonance reagents, deuterated reagents, by means of pumps represented by numeral 37. The trap 35 can release a held separated sample for nuclear magnetic resonance analysis.

In various embodiments, the trap 31 can include two or more separate traps (not shown). The separate traps can be used to hold multiple analytes of interest, for example in a queue for analysis. Such an arrangement would be particularly useful where separation of the sample proceeds much more quickly than analysts of a sample.

Nuclear magnetic resonance assembly 17 receives one or more separated samples defined by retention times and producing nuclear magnetic resonance data for the separation sample (or one or more separation samples). The nuclear magnetic resonance assembly comprises a NMR magnet and probe subassembly 41 and NMR console 43. The NMR console is a control unit for the NMR assembly 17. The NMR magnet and probe subassembly 41 is a subsystem with at least one end of the probe located within a very strong and highly homogeneous primary magnetic field (B_zero field), where the probe is RF-tuned to detect the magnetic resonance of protons, or potentially other atomic species, on the analyte molecule. A flow probe such as the MRM microcoil probe contemplated for use here, incorporates a very low volume (few microliter) flowcell having an inlet port and an outlet port. The inlet port is in fluid communication with the output of conduit 15. The outlet port can simply lead to a waste collection device, or can lead to a vial or well plate which can be used to recover sample for other purposes, as NMR detection is a substantially nondestructive technique.

A flow probe can eliminate the mechanical manipulations associated with transporting NMR tubes into and out of the interrogation region of the NMR spectrometer. Tube based NMR measurements are part of the original or classic mode of use, but to achieve online connectivity and concomitant throughput enhancements, a flow probe is a practical necessity. It allows the probe hardware to be installed once (and in many cases, to be shimmed just once), and not physically moved to perform subsequent analysis. Rather, only the solvated sample is conveyed into and out of the Interrogation region of the probe, using liquid flows derived from pumps. Such flows can be redirected, or stopped and started, using chromatography grade switching valves (discussed in further detail below).

Controller (also referred to herein as system controller) 19 is in signal communication with the closed chromatographic assembly 13, conduit 15 and the nuclear magnetic resonance assembly 17. Controller 19 receives retention time data and unclear magnetic resonance data and associates the retention time data and nuclear magnetic resonance data to at least one of the sample and the separated sample. The controller 19 is a computer or CPU and supporting software, firmware and instructions. The computer or CPU can be a personal computer, mainframe, server or integral with one or more assemblies of the device 11.

The device 11 further comprises at least one second detector in the form of mass spectrometer 47 and photodiode array CV absorbance ("PDA") detector 49. Each detector, mass spectrometer 47 and PDA detector 49, is in fluid communication with the conduit 15 and in signal communication with the controller 19. The second detector produces second detector data, and the controller associates the second detector data with the retention time data and nuclear magnetic resonance data to at least one of said sample and said separated sample.

A preferred device 11 uses the PDA detector 49 as a peak detector. The PDA detector 49 is in fluid communication with the conduit 15 and is in signal communication with the controller 19. Conduit 15 has a traction selection or slicing valve 51 in signal communication with controller 19 which works in conjunction with the controller 19 and the PDA detector to isolate peaks. The traction selection valve 51 has one or more sample holding loops 53 to nark or temporarily hold a peak of interest before discharging such peak to the trap 31.

PDA detector 49 produces one or more signals corresponding with an analyte of interest or a potential analyte of interest in a separated sample to isolate the separated sample to form an isolated separated sample. The PDA detector 49 signal prompts the controller 19 to direct the isolated separated sample to at least one of the nuclear magnetic resonance assembly 17 and mass detector 47. In various embodiments, fraction selection valve 51 receives the isolated separation sample and forms isolated separated sample aliquots, and directs at least one isolated separated sample aliquots to the nuclear magnetic resonance assembly 17 and the mass detector 47 such that said isolated separated sample aliquot is associated by controller with nuclear magnetic resonance data, the PDA detector data, the mass spectrometer data and retention time data.

With reference to FIG. 1, a hierarchical system control arrangement is shown, wherein a set of functional modules is implemented, each with its own embedded, real time controller (typically a microcontroller or microprocessor executing programmed instructions according to, and embodied within, embedded firmware). This set of functional modules is, in turn, responsive to a host or supervisory controller, most typically implemented as a computer workstation, which resides in electrical continuity (including wired and/or wireless communication) with the respective modules. The supervisory controller implements, via programmed software, the user interlace for the human operator, thus allowing an analyst to specify how a chromatography separation is to be accomplished, and now the resulting data streams and liquid tractions are to be treated and coordinated.

Importantly, this controlling interface includes, in a preferred embodiment, the assimilation of data streams from both a PDA detector, and a mass spectrometer of a selected architecture, which can, for convenience, be a bench top single stage quadrupole mass analyzer ("mass detector" or "MS"). These two analyte detection subsystems, responsive to the supervisory controller, provide the controller with a window upon the liquid phase separation, which is used to steer the actions taken by the fraction selection valve and by the other modules within the system, live integration of control at the supervisory level is critical to achieving closely coordinated action throughout the system, and will be seen as substantially fundamental to the execution of a full inline structure elucidation.

It will be recognized that, at the option of the user, the detector types indicated above can be replaced or augmented with other detector types as appropriate to the end use application intended by the user. Examples might be the substitution of an evaporative light scattering detector ("ELSD") or charged aerosol detector ("CAD") to better address analyte detection in situations where substantially no UV chromophore is present, or the substitution of a tandem mass spectrometer ("MS-MS") in place of, or augmenting, the single stage mass spectrometer described above. The tandem mass spectrometer can comprise one or more of any of the known mass spectrometer architectures (such as quadrupole mass analyzers, time of flight mass analyzers, sector analyzers. Ion cyclotron resonance analyzers, or others), and can include one or more collision chambers to augment analyte fragmentation between mass analyzer stages, as is known in the art. The mass spectrometer can farther implement one or more ion mobility spectrometry ("IMS") drift tubes between mass analyzer stages, to achieve further dimensions of resolution of analytes. Such mass spectrometers are manufactured by Waters Technologies Corporation, with commercially available examples being the Synapt G1 and G2 series of instruments.

At the left side of FIG. 1 is a first chromatography system, hereinafter referred to as the primary chromatography system, configured so as to carry out a complete chromatography separation, in that each of the following requisite functions is present: (1) non-deuterated (e.g., protonated) solvent gradient generation and delivery, (2) sample management including sample injection, (3) analyte separation on a column containing an appropriate stationary phase, (4) analyte detection mediated by a first and a second detection subsystem (UV-Visible absorbance detection and mass spectrometric detection, respectively, in this exemplary embodiment).

A sample is first maintained and then introduced by way of the sample manager within the primary chromatography system, which performs the injection of the commanded sample volume into the primary chromatography system mobile phase stream. Typically, in analytical chromatography, the sample volume is configured such that the sample mass injected is a small enough value to avoid overloading the capacity of the column, while being large enough that the sample components can be visualized with sufficient signal-to-noise at the detector(s). Depending upon the scale at which the primary chromatography separation is conducted, the analyte of interest may, or may not, be present in sufficient mass to accomplish the intended NMR spectroscopy based upon a single sample injection event (see below for sample accumulation functionality).

Intervening between the PDA detector and the mass detector is a four port flow splitter, such as that commercialized by Waters Technologies Corporation. Whereas the PDA detector, which is a substantially nondestructive analyte detector, experiences the through flow of the entirety of the mobile phase stream emerging from the separation column, the mass detector (which is a destructive analyte detector) sees or experiences only a minor proportion of that mobile phase stream (a split ratio of 15:1 is used in one exemplary embodiment, where only about 6% of the analytical mobile phase stream is directed to the mass detector. The balance of the flow, or about 94% of the analytical stream, is redirected to a different, selected outlet port.) The flow splitter includes a port for providing a makeup solvent flow, such that the minor percentage of analytical flow which is tapped from the analytical stream for mass spectral analysis is conveyed efficiently to the mass detector, and that the analyte arrives at the mass detector in a solvent environment which is optimized for the mode of mass spectrometric analysis being employed.

In the illustrative embodiment of FIG. 1, this makeup flow is sourced from a 515 pump module, which is compact and comparatively inexpensive. A representative flow rate sourced by this pump might be 0.20 mL per minute, although that value is not intended to be unique or limiting within this disclosure. The bulk of the mobile phase stream emerging from the analytical column and transiting the flow splitter is emitted from the splitter through a port which is in fluid communication with a rotary shear seal selection valve, also known in chromatography as a switching valve. This valve is indicated on FIG. 1 as AMAV1 ("automated motorized auxiliary valve #1"). When the detector(s) indicate to the system controller that the analyte of interest is not present in the mobile phase stream, this selection valve is oriented such that the mobile phase stream is directed to waste, without transiting the accumulator loop of AMAV1. Only when the detector(s) indicate(s) the presence of the analyte of interest, is AMAV1 transiently switched so as to capture the mobile phase stream into the accumulator loop volume, thereby arresting the analyte of interest within that loop. AMAV1 is also referred to herein as a fraction slicing valve, as a result of this functionality.

With the sample focusing capability resident in the downstream trapping arrangement, the AMAV1 loop volume can be selected to be multiple times the expected volume of an eluting chromatography peak, such that the analyte of interest resulting from multiple, serial chromatography separations can be accumulated there, prior to refocusing and entrance into the NMR spectrometer. This accumulation capability, followed by sample refocusing is, to our knowledge, a unique attribute of the instant invention. This accumulation capability speaks to matching the mass loading of the chromatography separation with the analyte mass requirements of the NMR spectrometer. The volume, geometry, particle size, and other properties of the packed bed used for analyte trapping can be quite different from those selected for the primary chromatography separation column. Those attributes of the trapping column will typically be selected to achieve a loading capacity consistent with the analyte mass needs of the NMR spectrometer. See also the foregoing discussion of the concept of impedance matching between LC separation and NMR analysis. The primary analytical column can be operated at sample loads which are less than that required by the NMR spectrometer, and that multiple instances of primary chromatography separation can be undertaken to accumulate the necessary mass of separated (fractionated) analyte within the accumulator loop at AMAV1.

In one preferred embodiment, the scale of the primary chromatography separation is chosen such that a single instance of elution of the analyte of interest is captured within the accumulator loop at AMAV1. In this case, accumulation corresponds to the isolation of substantially one chromatographic peak or band within that loop. Genetically, during the analyte accumulation phase of system operation, the pump module labeled "515 Loop Pump" is maintained at a flow rate of zero. Once the analyte accumulation phase is complete, the accumulator loop of AMAV1 will have been charged with analyte corresponding to the results of one or more primary chromatography separations. Expulsion of the loop contents is accomplished by switching AMAV1 to the state which places the accumulator loop on line with the 515 Loop Pump, and by providing a loop expulsion flow rate at the 515 Loop Pump. Consistent with the at-column dilution principles recited in U.S. Pat. No. 6,790,361 (incorporated herein by reference), an aqueous flow derived from the "515 Dilution Pump" is summed into the loop expulsion flow at the "At-column Dilution Tee" upstream of the trap column. Provision of this diluent reduces the solvating strength of the mobile phase and allows the analyte of interest to be chromatographically adsorbed or trapped on the reversed phase trapping column affixed to AMAV2 ("automated motorized auxiliary valve #2"). Advantageously, the properties of this diluent flow are modified to promote highly efficient trapping of the analyte of interest. For example, if the analyte resides as an acid in solution, the solution (the diluent mobile phase) can be acidified, through the use of a solvent modifier, to decrease the solubility of the analyte and promote the most efficient trapping behavior. Once the analyte is bound, or trapped, on or against the stationary phase, it is possible to eliminate the solvent modifier and wash the trapped analyte with, for example, neat $D_2O$. The goal of this washing is to condition the retained analyte into a regime most advantageous to support high quality NMR spectroscopy. In most cases, elimination of butters or other solvent modifiers is an important step toward achieving high quality NMR results. For the instant NMR application, the aqueous diluent flow can be further defined to comprise a deuterated aqueous flow (e.g., $D_2O$). This aqueous flow is provided over a timeframe such that the volume dispensed is sufficient to convey the analyte toward and onto the trap column, and further to rinse or flush the trap column to remove $H_2O$ and substitute it with $D_2O$.

Provision of an aqueous diluent at the at-column dilution tee is consistent with a reversed phase mode of trapping at the trap column per U.S. Pat. No. 6,790,361, although other modes of analyte trapping such as normal phase trapping are contemplated. The loop expulsion and analyte trapping operation is allowed to proceed until the entire loop volume at AMAV1 has been fully flushed. Accomplished under system control, this process results in the analyte of interest being focused substantially at the head of the trapping column. In the process of trapping, the analyte can have been transported some measurable distance from the chromatography system toward the NMR flow probe entrance port. This transport step can be achieved with substantially no zone broadening impact, as the trapping process exerts a pronounced refocusing effect upon the analyte.

During the trapping process, the liquid stream bearing the analyte and the diluent transits the trap column and emerges from AMAV2 to waste. Also in a first preferred embodiment, during the trapping process, the deuterated organic pump B belonging to the Deuterated Gradient Binary Solvent Manager ("Deuterated BSM") is actuated to achieve a nonzero flow rate, such that the fluid path intervening between AMAV2 and the outlet of the NMR flow probe is prefilled with the deuterated organic phase, in preparation for analyte elation from the trap.

After the trapping phase is completed, the loon pump and the at column dilution pump are respectively brought to the zero flow state. Typically, the deuterated organic pump is also brought to a zero flow state at this time. AMAV2 is then switched to the position which places the trapping column in fluid communication with the deuterated gradient BSM and with the NMR flow probe. Under system control, the deuterated gradient BSM organic pump is then actuated to deliver deuterated organic solvent in a volume as required to elute the analyte off the trap and to transport the analyte to the NMR detection cell. Once that volume has been delivered, the pump flow is arrested, causing the analyte peak to be parked in the NMR cell.

It is an option to incorporate an additional valve at the outlet of the NMR flow probe, such that coasting or skidding of the analyte peak during the parking process is substantially avoided. Skidding can arise from the relaxation or decompression of previously compressed volumes of solvent (compressed during delivery of liquid through the trap and associated tubing). The use of a controllable valve to block flow at the exit of the NMR flow probe can be advantageous to arrest this skidding response, thereby improving the positioning accuracy of the nark. Also, where the term deuterated organic solvent appears above, that solvent can indeed be neat deuterated organic solvent, such as DMSO-d6 or $CD_3CN$, or it can be an organic or an organic aqueous deuterated mixture which has sufficient solvating strength to elate the analyte of Interest from the trap column in a substantially sharp zone or band. The use of a gradient BSM at this location in the system facilitates selection of a desired solvating composition, under program control. In many cases, the neat deuterated organic can be most desirable for this purpose, but options and alternatives exist, and can be programmed into use by the analyst.

Once the analyte of interest is parked within the interrogated region of the NMR flow cell, the NMR controller can undertake shimming, followed by spectral acquisition and post-processing. Known NMR controllers have the ability to accumulate spectra for the period of time necessary to achieve a desired S/N ratio, and to perform a variety of post-processing steps. Some or all of the post-processing which is accomplished after spectral acquisition can occur within the host workstation.

Preferably, the host workstation which is the supervisory controller for all of the foregoing operations, has a scope of analysis which is broad enough to assimilate at least UV spectral data, mass spectral data, and NMR spectral data (and potentially other data streams as well), and to coordinate the reporting of that data to a software functionality that can provide structure elucidation along with a confidence level, as the output of the analysis, finlike prior art approaches to the preparation and handling of samples for NMR spectroscopy, which can involve many manual transfers and manual or semi-automated processing steps, and can occupy multiple systems in different locations, an integrated and fully automated system can provide a traceable trail which connects a relatively raw incoming sample mixture with a finished output such as an elucidated structure or absolute compound identification.

Figure 2:
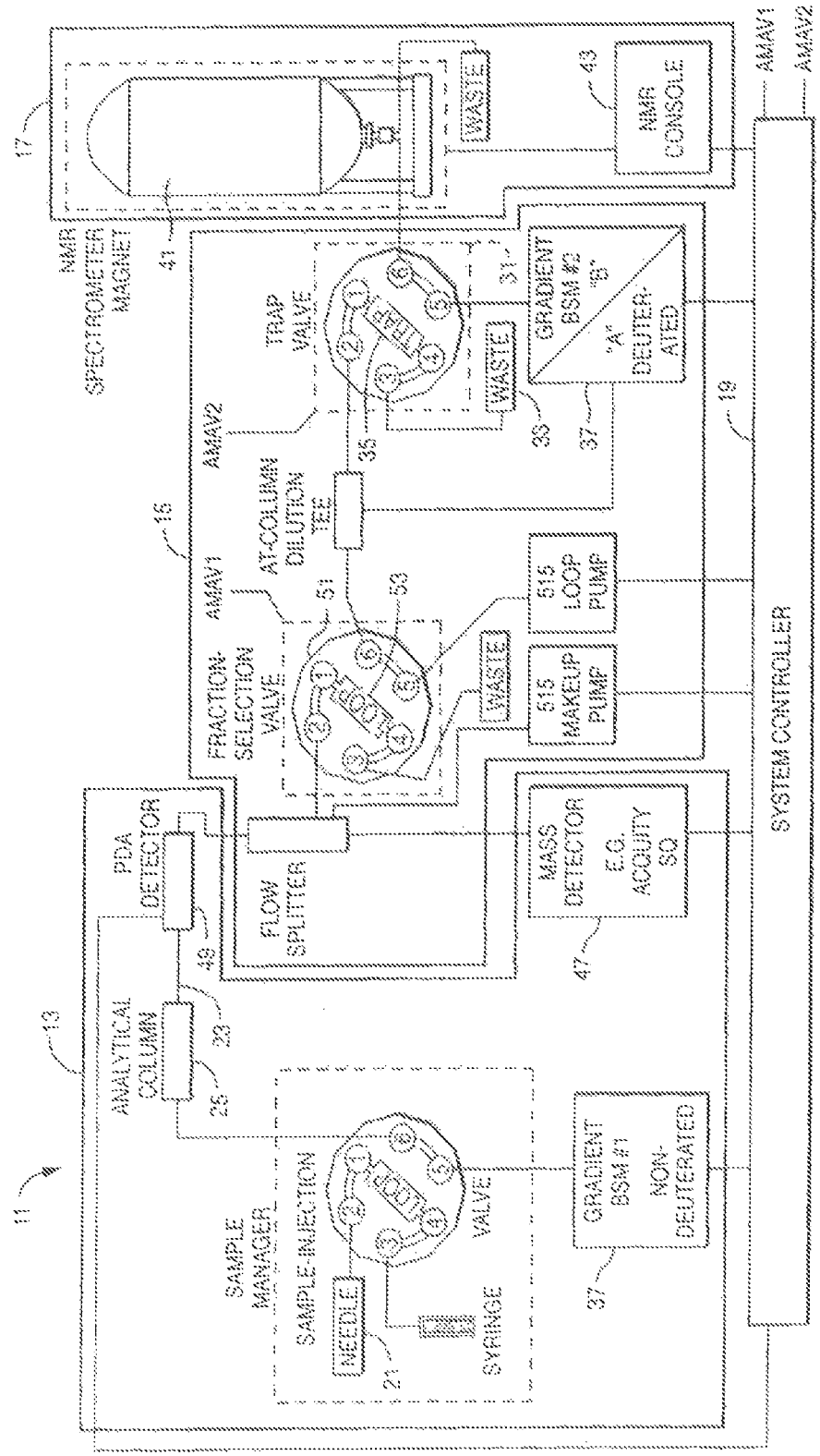
FIG. 2 depicts, in schematic form, another example device incorporating features of the present invention.

Changes to the system configuration depicted in FIG. 1 can be contemplated while remaining within the spirit and scope of the instant invention. One such change is depicted in FIG. 2. In the system of FIG. 2, the module indicated as "515 Dilution Pump" has been removed, and its function replaced by pump A of the deuterated Gradient BSM #2. This change eliminates one hardware module, thus making the system slightly less complex, or slightly less expensive to implement. The change, however, implies that pump B of the deuterated Gradient BSM will be used exclusively to elute the analyte from the trap column (e.g., blended solvent mixtures produced by the coordinated actions of pumps A and B of the deuterated Gradient BSM will not be available by program to elute sample from the trapping column.) For many applications, a neat organic solvent delivered by pump B can be quite acceptable for this elation task, or a pre-blended solution which is delivered solely by pump B can be used.

In an era of fast chromatography, particularly chromatography which is fast relative to the anticipated NMR acquisition time, it can be of significant interest to accumulate analyte from multiple (typically sequential) primary chromatography separations, derived from respective instances of sample injection, and to efficiently co-add the separated (fractionated) analyte material to produce the purified, concentrated sample mass required for NMR analysis. In this way, the sample mass and/or sample volume limitations of the primary chromatography separation can be respected, so as to deliver a usefully high quality separation which preserves the available chromatographic resolution. Maintaining chromatographic resolution is an Important contributor to maximizing the purity of the collected fraction, and thereby minimizing background signal at the NMR unrelated to the analyte of interest. It has been stated in the foregoing description that the analytical system of FIG. 1 or of FIG. 2 can be configured and operated in a mode where the accumulator loop at AMAV1 is sized to accumulate analyte from multiple, sequential, primary chromatography separations. It will be recognized that an accumulator loop has a finite volume, which determines an upper bound on the number of primary chromatography separations from which analyte can be extracted or fractionated. In the case of relatively dilute analyte solutions, increased analyte mass can still be desired, even when the accumulator loop is filled (from a volume standpoint). Overfilling the accumulator loop results in direct analyte loss to waste, which is undesirable. In a preferred embodiment, the system of FIG. 1 or of FIG. 2 can be operated such that when the accumulator loop at AMAV1 is filled (from a volume standpoint), the system controller undertakes a trapping operation which focuses and retains the analyte, while directing the solvent volume to waste. It will be recognized that while the trapping column has a finite trapping capacity which relates to the analyte mass applied, the trap can process or throughput an almost arbitrarily large volume of liquid solvent, thereby substantially overcoming the volume limitation of the accumulator loop at AMAV1. Once analyte trapping is accomplished, the accumulator loop at AMAV1 is effectively restored to its empty state, and is ready to receive new aliquots of analyte from the primary chromatography system. Particularly in the case of environmental analysis, where the analyte of interest can reside at a low level within the environmental primary chromatography sample, multiple cycles of accumulate-and-trap can be carried out, such that the trapping column is taken close to its saturation capacity of analyte. Again, the trap column geometry and stationary phase are selected to optimally match the analyte mass requirements of the NMR spectrometer. This approach can achieve a substantial degree of decoupling between the scale of the primary chromatography separation and the analyte requirements of the NMR spectrometer. This substantial decoupling can itself overcome one of the perceived limitations to accomplishing the hyphenation of chromatography with NMR spectroscopy. It will be readily apparent that within the spirit and scope of the instant invention, it is an option to perform either: (a) multiple analyte accumulations at the AMAV1 loop, followed by a trap event, or (b) single analyte accumulations at the AMAV1 loop, each followed by a respective trap event, or (c) any combination of (a) and (b), as specified by the user. It should also be noted that there are chromatography conditions which must be met in order to achieve highly efficient sample aggregation at the trap (e.g., minimizing sample loss or breakthrough at the trap), in concert with efficient sample focusing.

In a recent scientific publication (Sandvoss et al., Magn. Reson. Chem. 2005; 43: 762 770) the authors recited an approach where a threefold excess of water (unmodified water) was added to a chromatographic eluent stream in order to attempt to trap analyte on HySphere Resin GP (general purpose polydivinylbenzene based resin) cartridges. These authors documented at length problems which they encountered in obtaining sample aggregation in multiple trapping instances. Also, they pointed out that "as the polarity of the compounds increases, the efficiency of the multiple trapping decreases." As the eight authors of this paper practice within the sphere of pharmaceutical industry analysis, one might accept these findings as indicative of the current "state of the art." It will be noted that in the instant invention, highly efficient sample aggregation and a substantial absence of trap breakthrough has been confirmed using appropriate in line detectors, and those behaviors arise as a consequence of careful attention being paid to the following details. First, a very highly retentive stationary phase (e.g., Oasis™ HLB, Waters Technologies Corporation, Milford, Mass. USA) is incorporated into the trapping column. Second, appropriate selection of mobile phase modifiers for the diluent stream feeding the at-column dilution tee is made, in order to optimize trapping behavior beyond what would be achieved through the use of neat $H_2O$ or $D_2O$. Third, the ratio of diluent flow rate to analyte flow rate must be extreme enough to ensure that trapping is accomplished (e.g., local solvating strength is reduced sufficiently), independent of the solvent environment from which the analyte was initially sliced. One should recognize that when analyte is sliced from its elation position within the primary chromatogram a sampling of the instantaneous mobile phase condition (in which that elation occurred) is likewise captured into the slice valve loop. That mobile phase condition accompanies the analyte along the path toward the at-column dilution tee. The diluent addition, and the at-column dilution tee geometry, must both be selected to achieve the necessary redaction in solvent strength to allow the analyte to be refocused and trapped on the trap bed, independent of the location within the primary chromatogram (e.g., the local solvent environment) from which the analyte was sliced. A failure to produce sample aggregation (as documented in Sandvoss et al.) is a measure of the failure to achieve a chromatographic trapping condition at the trap column. When trapping conditions are satisfied, the trap works properly, and analyte aggregation and refocusing result.

Preferably, all of the capacity of the stationary phase within the trapping column is available for retention of the substantially purified analyte of interest, in contrast to the situation at the primary chromatography column, where a substantially cruder sample mixture is applied, and where the analyte of interest can represent only a minor component of the totality of the material applied during primary chromatography sample injection.

Figure 3:
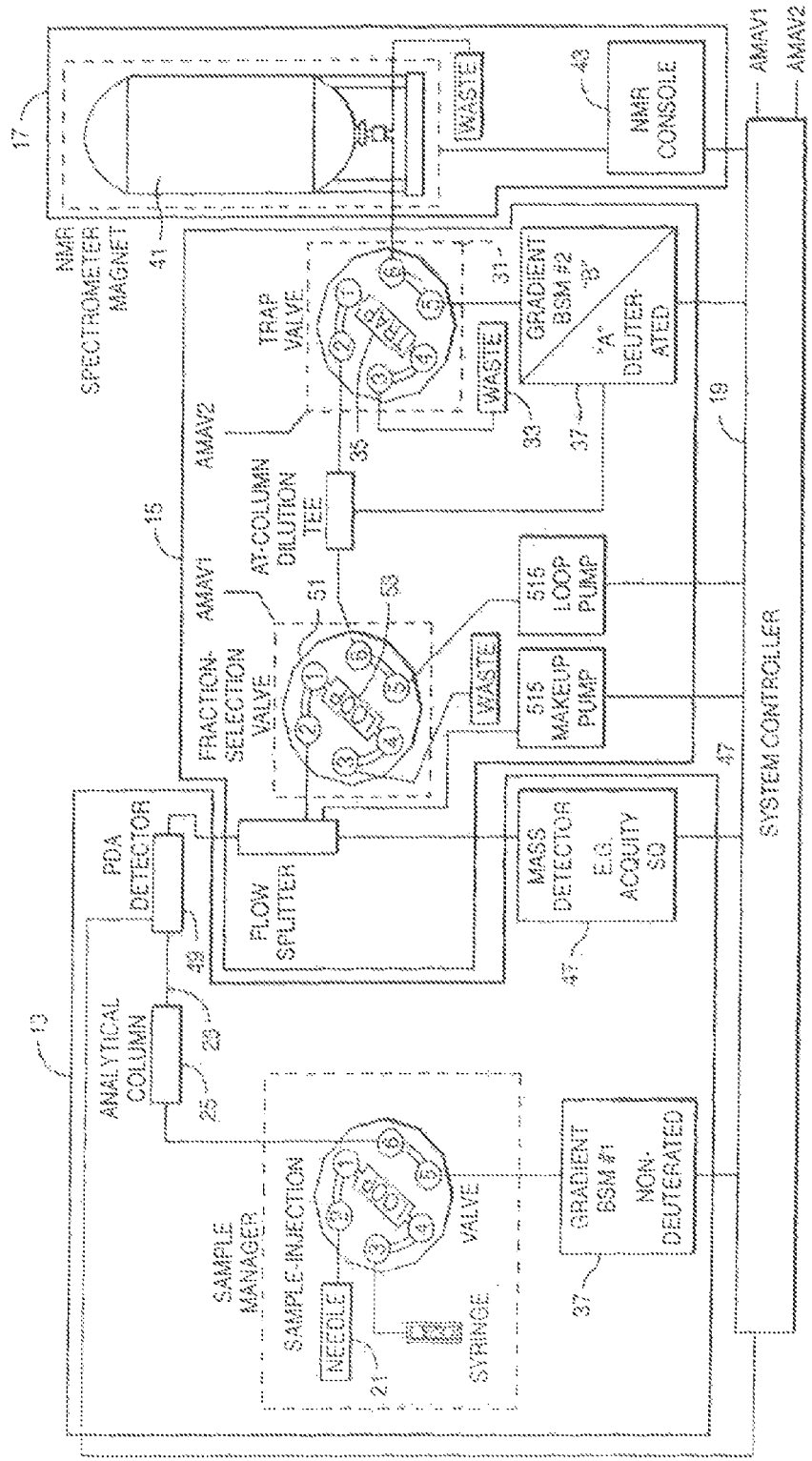
FIG. 3 depicts, in schematic form, yet another example device incorporating features of the present invention.

With regard to FIG. 3, a system is shown which extends or augments the system of FIG. 2 with an additional module comprising rotary shear seal valves and a plurality of external loops for respective analyte accumulations. It will be recognized that the system of FIG. 2, which implements a single analyte accumulator loop at AMAV1, will typically be limited to accumulating only a single analyte species, from a single peak of interest, from a single or from multiple primary chromatography separations, if multiple primary chromatography separations are performed sequentially, typically the same analyte species will be accumulated from the same peak of interest within each of N respective primary separations. However, analytical scenarios are readily anticipated where multiple peaks of interest can be present within a primary chromatography separation, and where the co-addition of different analyte types within a single accumulator loop is highly undesirable.

In such scenarios, an augmented analyte redirection and analyte accumulation capability as implemented in FIG. 3 can be usefully employed. The functionality depicted within the added module corresponds to that of a 1-of-N multiplexer/demultiplexer arrangement, which inserts fluidically into the system of FIG. 3 at AMAV1 ports 1 and 4, respectively, thereby replacing the single loop which would otherwise be shown connecting that pair or locations. The rotary shear seal valves of the multiplexer/demultiplexer are constructed so as to allow a single fluid port, positioned at the center of the valve stator, to be selectably placed in fluid communication with any 1-of-N ports radially disposed about the center of the stator. At the fluid entrance side of the arrangement (the demultiplexer), this construction allows an incoming fluid stream to be redirected to any 1-of-N separate analyte accumulator loops. At the fluid exit side of the arrangement (the multiplexer), tins construction allows a selectable 1-of-N analyte accumulator loops to exhaust fluid toward a single exit port. The terms multiplexer and demultiplexer are drawn from the corresponding functionalities which are known from digital electronics. Overall, the coordinated action of the demultiplexing and multiplexing valves allows a selectable 1-of-N analyte accumulator loops to be placed online for analyte accumulation, at the command of the supervisory controller. As that supervisory controller is assimilating data streams from the several detector types, it can intelligently determine which of the N available accumulator loops is selected to accumulate a particular peak within the primary chromatography separation, in this way, multiple peaks can be isolated and accumulated into respective accumulation loops, from a single primary chromatography separation, or from a series of primary chromatography separations. These respective analyte accumulations will remain separate and distinct, and can be analyzed sequentially by the NMR spectrometer, in successive, distinct cycles of loop expulsion and analyte trapping.

Figure 6A:
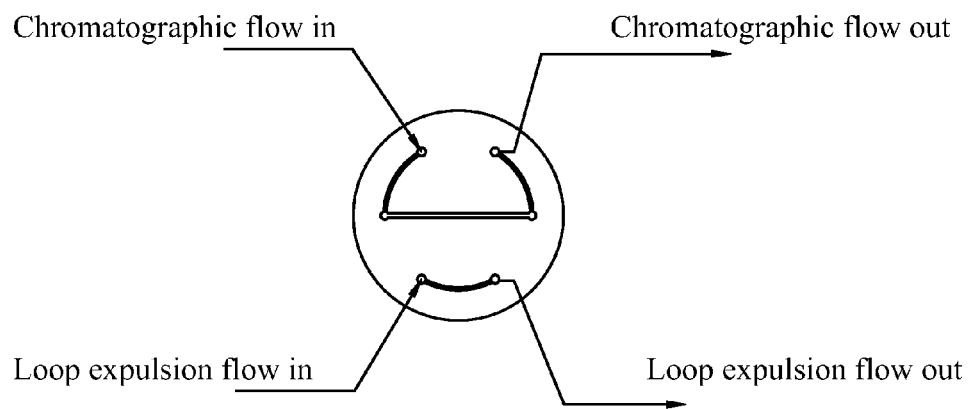
FIGS. 6A-D depict an example fraction selection valve and sample collection loop in accordance with the invention.
Figure 6B:
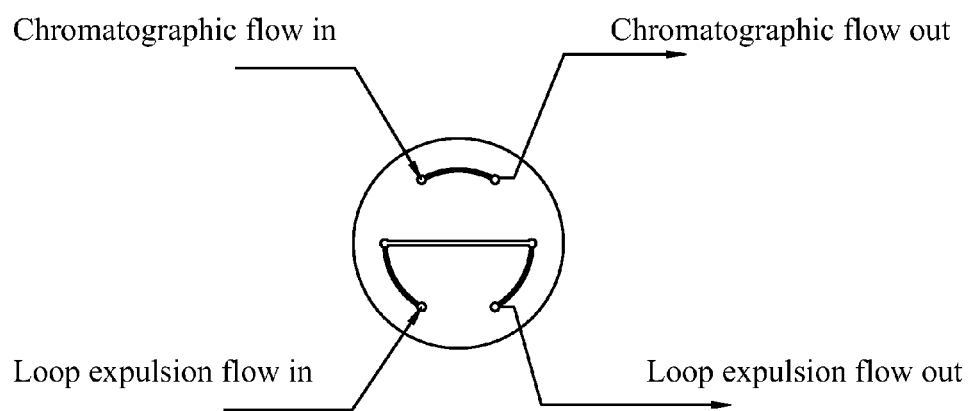
Figure 6C:
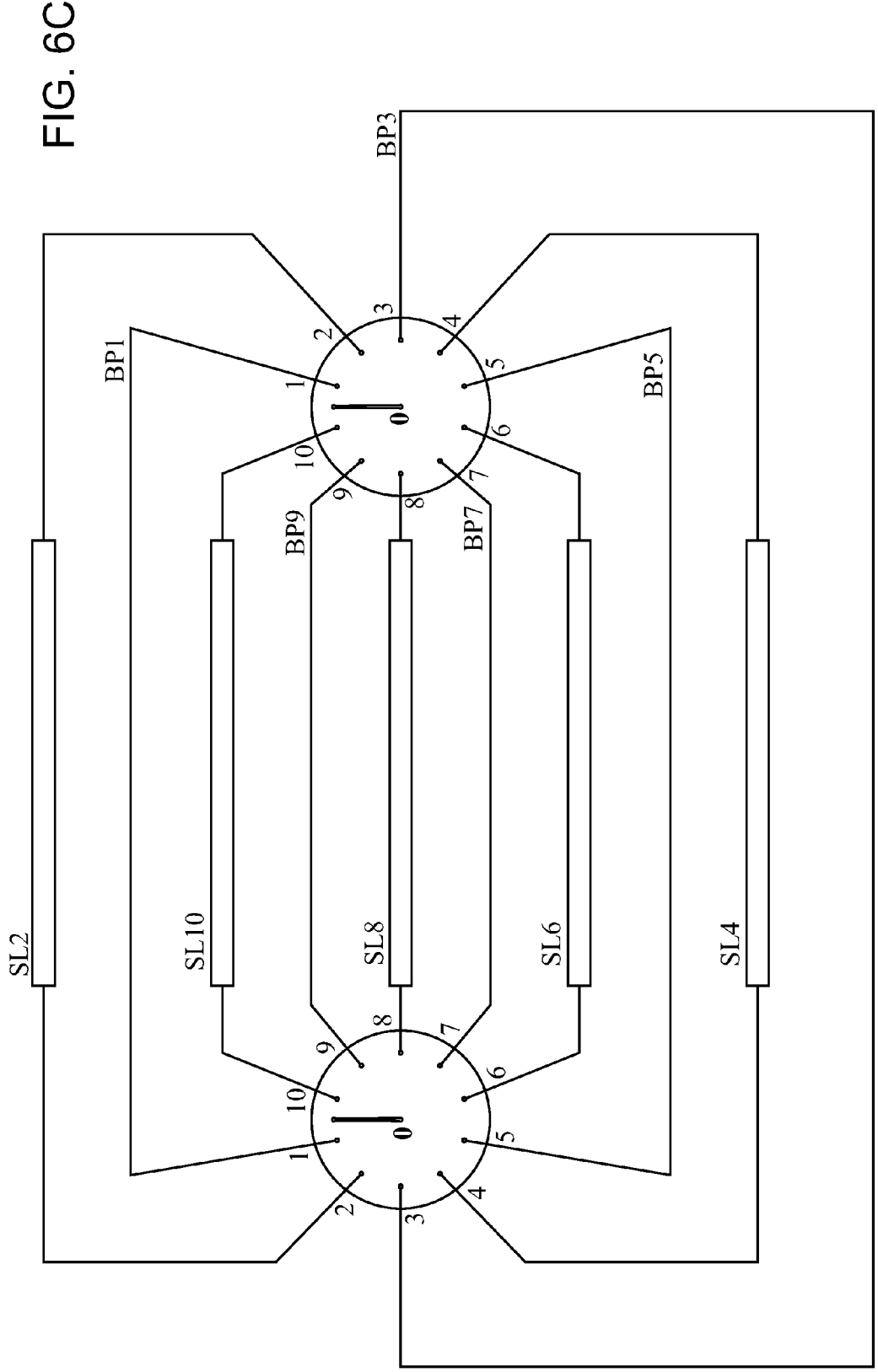
Figure 6D:
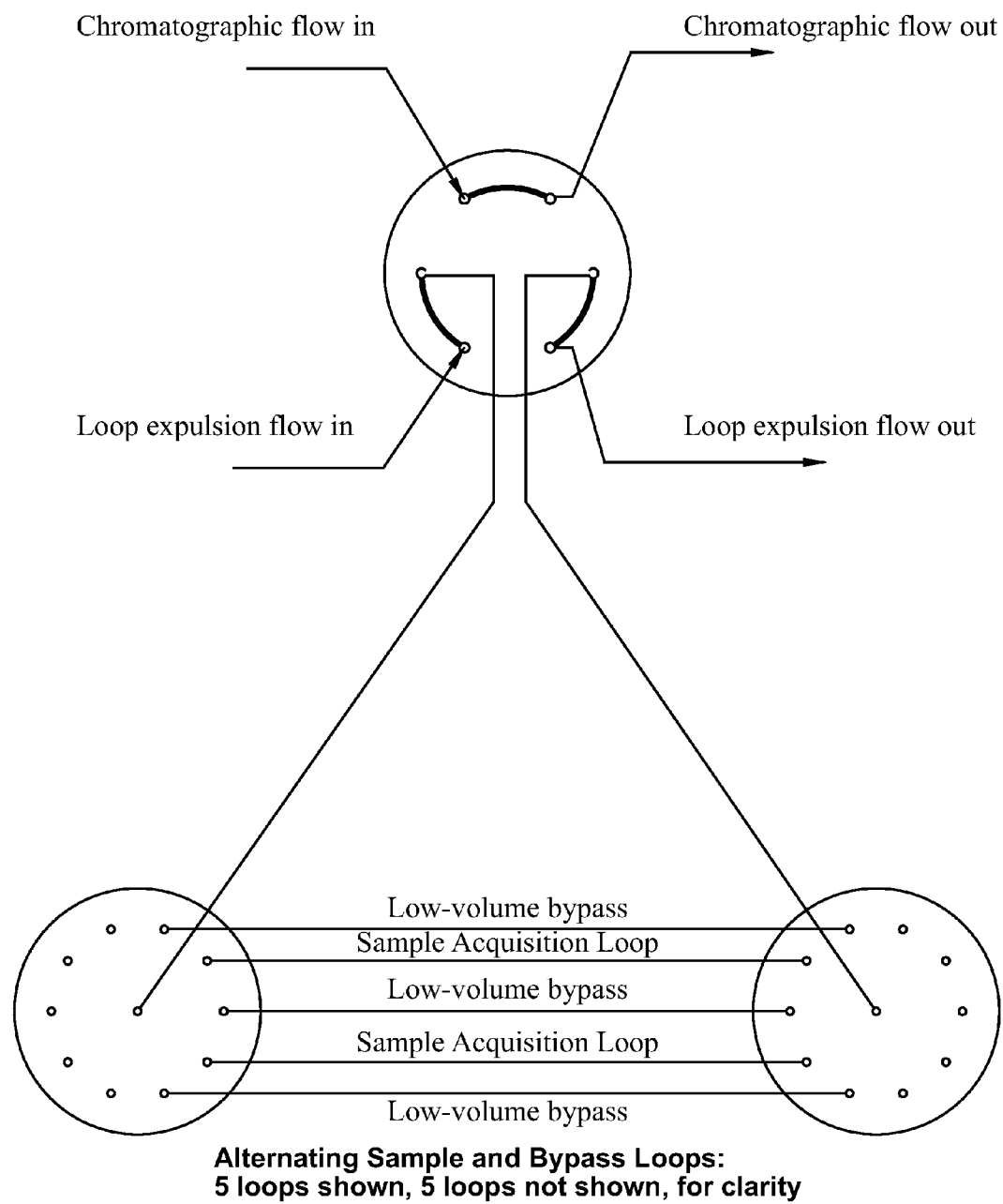

FIG. 6C (discussed in further detail below) depicts the alternation of bypass loops with sample storage loops, to accomplish "clean" or carryover-free sampling of multiple analytes from a chromatographic stream. This is a significant improvement over the behavior attainable with earlier system implementations.

Figure 4:
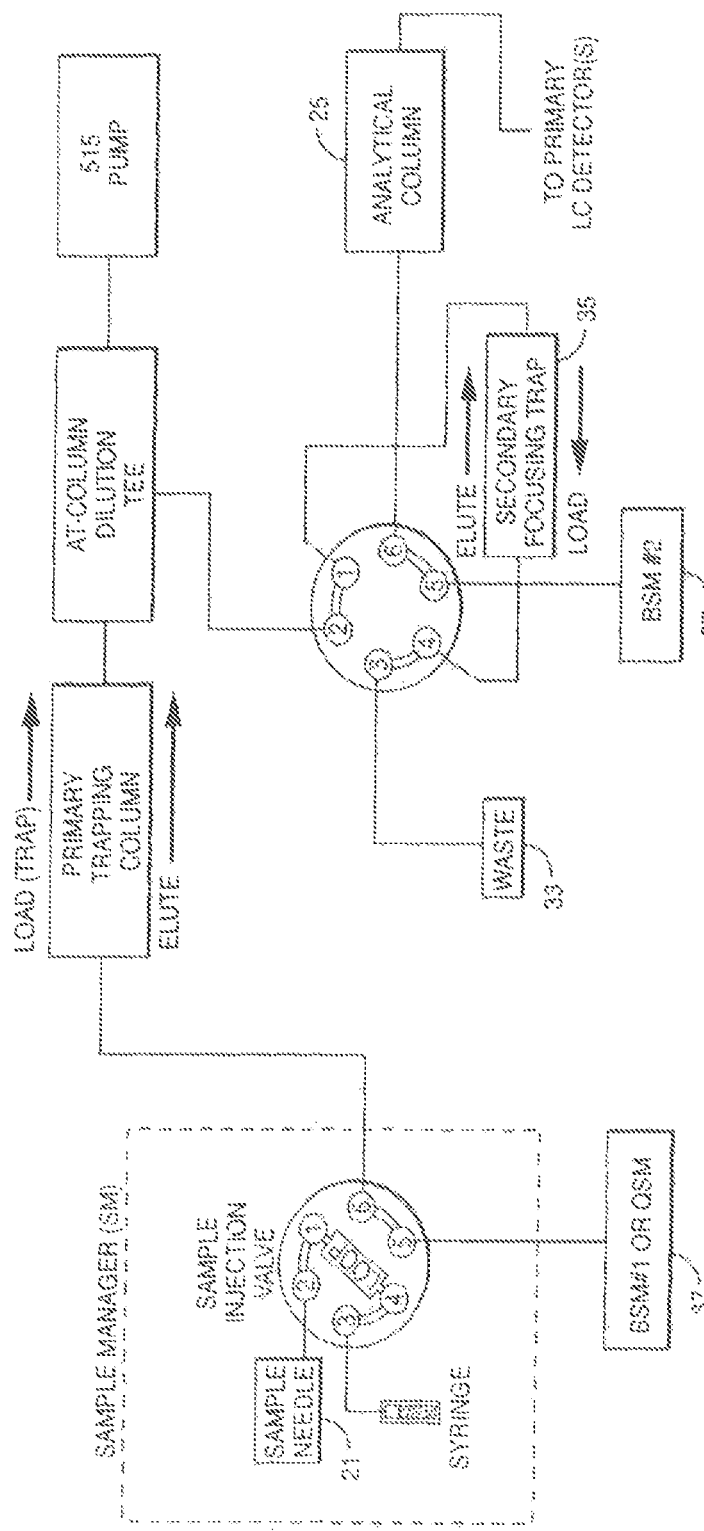
FIG. 4 depicts, in schematic form, still yet another example device incorporating features of the present invention.

With reference to FIG. 4, an alternate embodiment of the primary chromatography system is shown. The functionality depicted in FIG. 4 can be inserted, in a substantially modular manner, into the systems of any of FIG. 1 through FIG. 3, inclusive. FIG. 4 depicts a primary chromatography system which is configured to enable the focusing (and thus concentration) of dilute incoming samples, as might be required to perform certain environmental analyses. In an analytical scenario where the analyte of interest is a trace component within, for example, a water sample, it can be necessary to process a relatively large volume of that water sample in order to acquire enough analyte to carry out the intended analysis. In the primary chromatography system of FIG. 4, a primary trapping column is shown, the purpose of which is to achieve a first coarse step of concentration of analyte. Other materials present within the incoming sample can also undergo concentration at the primary trap, and will be separated from the analyte of interest in subsequent stages of chromatography. The primary trapping column incorporates a single fluid flow direction for both loading (trapping) and for elution, in the embodiment pictured. The terminology of "forward trapping, forward elution" is often associated with tins configuration. A secondary focusing trap column is shown, which incorporates a preferred bidirectional fluid flow configuration, where elution is accomplished in the reverse direction from trapping ("forward trapping, back elution"), through the use of a switching valve, it will be recognized that elution of sample from the primary trap requires a transient increase in the solvating strength of the eluent delivered by BSM #1. The module depicted at BSM #1 can, alternatively, be a quaternary solvent manager ("QSM"), thereby providing more alternatives to increasing the solvating strength of the eluent stream delivered to the primary trapping column. Correspondingly, the functionality indicated at BSM #2 could be supplanted by a QSM. The at-column dilution tee and 515 pump module shown are responsible for reducing the solvating strength of the eluent stream emerging from the primary trapping column, in order that the material released from the primary trap can be re focused on the secondary focusing trap. At either of the trapping stages, sample material which is not trapped, along with the incoming solvent, is directed to waste. The back elution which occurs at the second focusing trap can contribute to better chromatographic resolution in the primary chromatography separation, which is brought about, by BSM #2 acting in concert with the analytical column, in a system corresponding to that of FIG. 4, the primary trapping column can foe a relatively low pressure device such as an Oasis™ cartridge, as the primary sample trapping occurs separately from the primary chromatography separation (e.g., it is a separable process antecedent to primary chromatography). In contrast, the secondary focusing trap must be constructed to withstand the frill operating conditions extant during primary chromatography, as this trap will participate directly in that process. This system configuration enables efficient and automated processing of relatively dilute (and correspondingly, relatively large liquid volume) incoming samples as might be encountered in the environmental analysis realm.

Figure 5A:
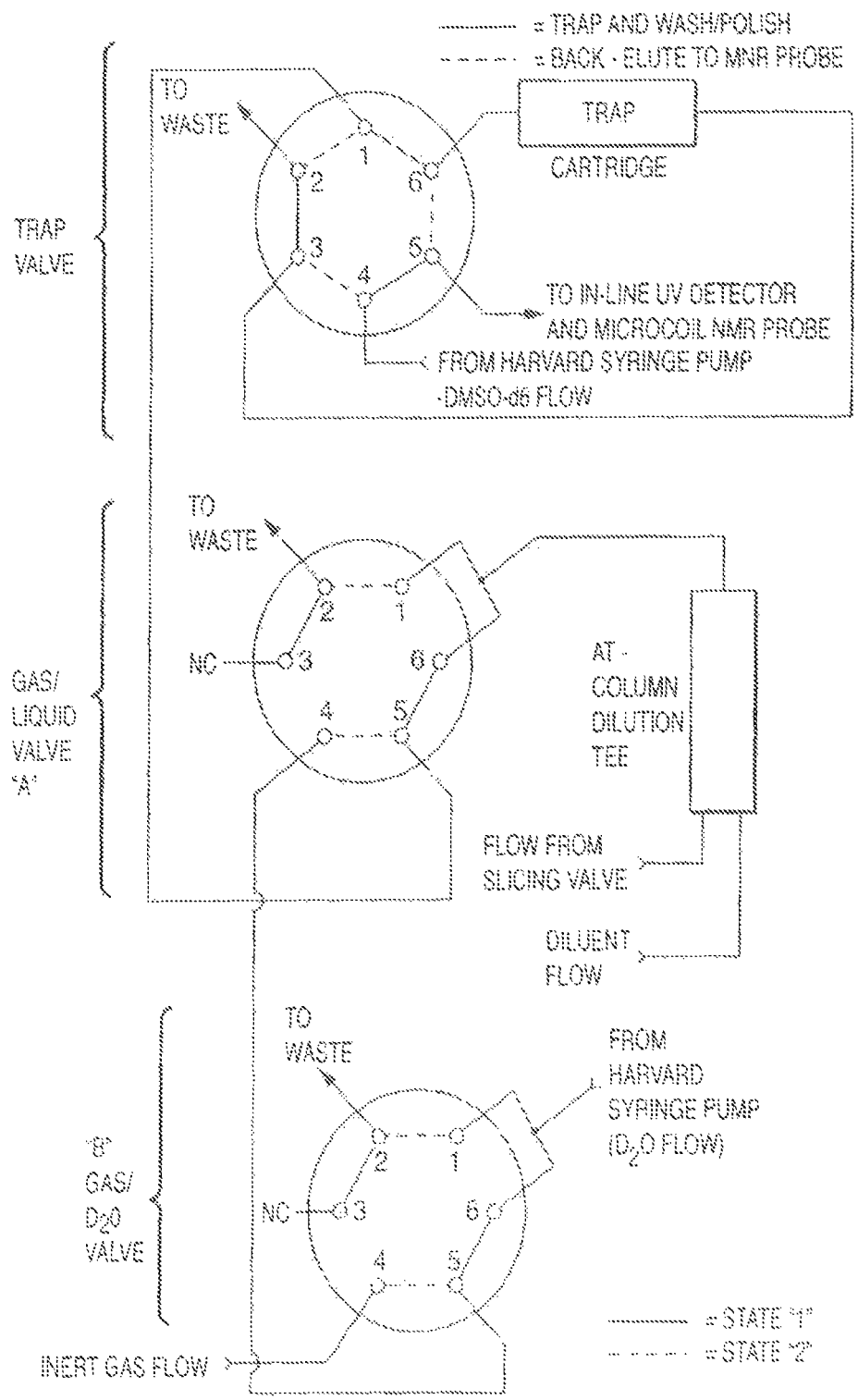
FIGS. 5A-C depict, in schematic form, example valve component and fluidic interconnections, which can be used to implement conduit 15 in the context of the system of FIG. 1.
Figure 5B:
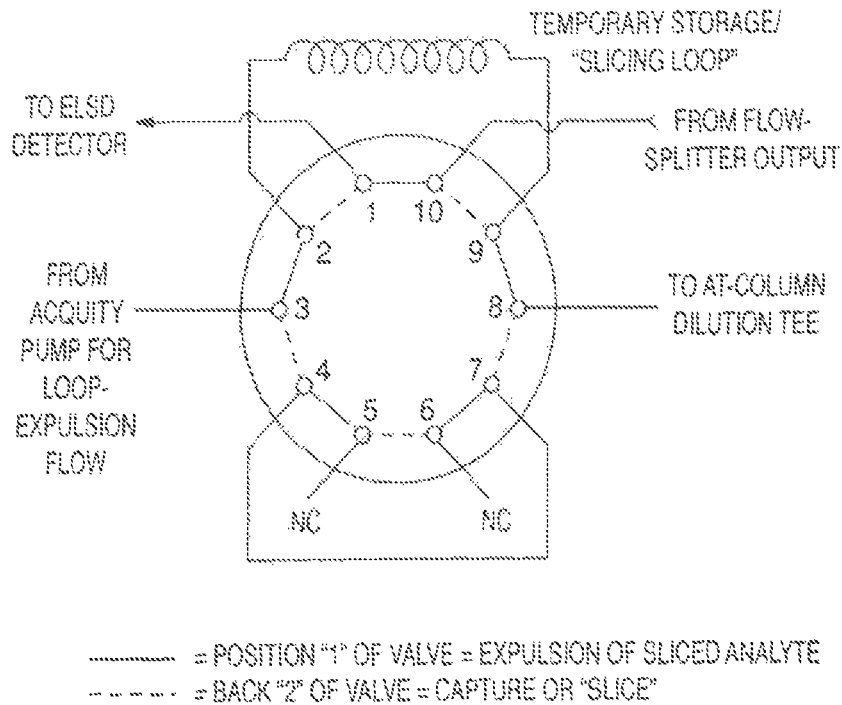
Figure 5C:
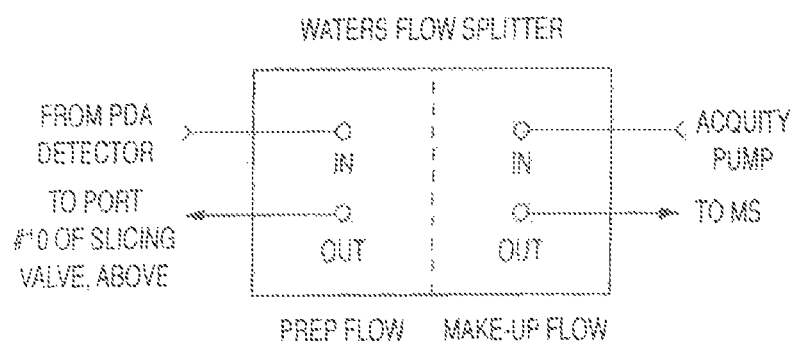

With reference to FIGS. 5A and 5B, valve components and fluidic interconnections are shown, which comprise a preferred embodiment for the implementation of conduit 15 as introduced in the context of the system of FIG. 1. This preferred embodiment is optimized to achieve the impedance-matching behavior discussed above. In FIG. 5A, a trap valve corresponding to AMAV2 of FIG. 1 is depicted along with a trapping column or cartridge. The trap valve shown is of a six port, rotary shear seal design as is known in the art. The rotor in this valve incorporates 3 distinct etched pathways, and commutates between two distinct states, as illustrated by the three solid and three dashed lines. Two supplementary valves are also depicted in FIG. 5A, these being referred to respectively as a "gas/liquid valve," and a "gas/$D_2O$ valve." While these valves are also of a rotary shear seal design, and incorporate 6 ports each, they differ from the trap valve in one important respect. These latter two valves are constructed with rotors which incorporate only two etched pathways, and which commutate between two distinct states. This construction is illustrated by the two solid lines and two dashed lines. This valve construction is known in the art as a dual diverter type valve. Also shown in FIG. 5A is an at-column dilution tee, which allows at least two input flow streams to be summed at the entrance side of the tee, and optimally includes a mixing functionality such as a porous bed packed with glass or ceramic beads or spheres. The function of this at-column dilution tee is to blend a diluent stream with a chromatographic stream in order to achieve a significant reduction in the solvating strength of the chromatographic stream. The purpose of this reduction in solvent strength is to achieve retention of an analyte on a chromatographic bed, typically after that analyte has been released from a chromatographic bed located upstream from the at-column dilution tee.

With reference to FIG. 5B, a fraction selection valve is shown. In this illustrative embodiment, the fraction selection valve is implemented as a 10 port, rotary shear seal type, as is known in the art. Also shown in FIG. 5B is a flow splitter and its respective connections to other modules in the system.

The sequence of operation, and the significance, of the components illustrated collectively in FIGS. 5A and 5B. The traction selection valve has a normal rotor position or valve state of 1, as illustrated by the solid interconnect lines. In this state, a chromatographic stream emerging from the flow splitter simply transits the valve, entering at port 10 and exiting at port 1 respectively. No fraction collection or slicing of analyte from the chromatographic stream is accomplished with the valve in this state. When this valve is commanded into state 2, illustrated by the dashed interconnect lines, the How path through the valve changes such that the chromatographic stream now transits the temporary storage or slicing loop. That is, the flow which enters me valve at port 10 emerges at port 9, enters the loop and transits the loop, reentering the valve at port 2, and exiting the valve at port 1. When the traction selection valve is actuated only transiently into state 2, as guided by the in system detectors, the effect is to capture or store a narrow region of the chromatogram into the temporary storage loop. The term slicing is used because a narrow region of the primary chromatogram has been sliced out, so as to be available for processing elsewhere within the system. The contents of the temporary storage loop remain in place within the loop if the loop expulsion pump connected to port 3 of the fraction selection valve is held or maintained at a flow rate of zero. When the system controller dictates that analyte trapping is to commence, the loop expulsion pump is provided with a nonzero flow rate while the traction slicing valve is maintained in state 1, causing the sliced traction to be migrated out of the temporary storage loop, exiting the valve at port 8 and proceeding to the at-column dilution tee of FIG. 5A. Diluent flow, typically in meaningful excess over the loop expulsion flow, is enabled to the diluent input of the at-column dilution tee. Referring to FIG. 5A, with the gas/liquid valve maintained in state 2, and with the trap valve maintained in state TRAP, the diluted stream bearing the analyte of interest is conveyed to the trap cartridge, where the analyte is substantially retained. Again, the diluent flow which is provided in excess can be configured with modifiers selected so as to improve or maximize the trapping behavior at the trap column. When the analyte trapping phase has run to completion, typically under time-programmed control, the loop expulsion flow and the diluent flow are typically reset to zero.

The phase of operation referred to herein as sample polishing will now be discussed. Analyte currently resident in the trap column exists in a protonated solvent environment, which can include modifiers such as boilers, salts, and the like. With the gas/liquid valve transitioned to state 1, the gas/$D_2O$ valve can be employed to allow replacement of the modified, protonated solvent environment with a deuterated environment substantially free of modifiers. That sequence is detailed immediately below. With the gas/$D_2O$ valve in state 1, a flow of dry, inert gas is enabled to the trap column, substantially expelling the protonated solvent from the void volume of the trap bed, to waste, finder time-programmed control, it is at the option of the operator to simply expel liquid from the void volume, or, with a more prolonged gas flow, begin to take the bed toward a state of dryness, in a preferred embodiment, the trap bed is not taken to dryness, but is simply purged of any bulk amount of protonated solvent (e.g., protonated solvent is generally expelled from the void volume of the bed).

Once this expulsion is accomplished, the gas/$D_2O$ valve is transitioned to state 2, allowing a now of deuterium oxide to traverse the trap bed to waste, in a preferred embodiment, this deuterium oxide flow is provided by a syringe based infusion pump such those produced commercially by Harvard Apparatus Inc. (Holliston, Mass., USA) under the model designation PHD. It will be noted that unlike larger volume, continuous flow pumps such as chromatography pumps, which are typically constructed with solvent reservoirs and lengthy inlet tubing lines which can be permeable to atmospheric contaminant species such as water molecules, a glass barreled syringe pump allows for fresh deuterated solvent to be taken up directly from a previously sealed glass ampoule as snipped by the supplier, and quickly encapsulated with the glass syringe environment. This absolutely minimizes exposure of the deuterium oxide or other deuterated species to water proton contamination, improving the quality of the analyte deuteration process. The volume of the glass ampoules in which deuterated solvents cars be ordered can be chosen so as to match the syringe barrel volume on the syringe pump, so that a single use/single filling is achieved, and there is no need to reseal ampoules after opening. This onetime use procedure maintains a very high quality of the deuterated phase, and is preferable for routinely achieving high quality NMR spectroscopy. Once a glass ampoule has been cracked open, typically only a few seconds elapse before the deuterated solvent contents are safely encapsulated within the glass syringe barrel of a Harvard type syringe pump. The piston seals on such a pump are typically Teflon, but the seal is labyrinthine enough that in practice, there is negligible gas transfer between the external environment and the interior of the syringe. Because the trap bed volume is so small, the flow rates and solvent volumes used to deuterate that environment are correspondingly small, and thus a syringe volume can last for at least a full day of operation, which is convenient for the user. By perfusing the trap bed to waste with deuterium oxide ($D_2O$), salts or other modifiers are solubilized away, and likewise water protons which can reside in the pore volume of the bed are equilibrated away.

It is at the option of the operator, under programmatic control, to incorporate as few or as many cycles of gas purging, followed by $D_2O$ purging, as are necessary or consistent with the quality of the desired NMR spectroscopy. It is our experience that retained analyte can be polished in this way to a quality which is only limited by the quality of the incoming deuterated phases. Typically such phases are purchased to a specification which includes the residual proton contamination present. The lowest levels of proton contamination are typically associated with a higher quality, and somewhat higher cost, reagent. The quality of that reagent thus can be more or less directly translated into a reduction of proton background in the resulting NMR spectroscopy. The use of an analyte polishing sequence, to remove salts or other mobile phase modifiers, typically also has a direct and measurable result on the NMR spectral quality with respect to freedom from artifacts.

After purging, but prior to polishing, the trap bed can be dried. In various embodiments, drying is accomplished by vacuum drying of the trap bed, typically with scavenging gas flow present. In various embodiments, drying is the final step of polishing, prior to analyte elation.

When such polishing is completed, it is at the option of the operator, under programmatic control, to cause the trapped analyte to be edited to the NMR microcoil flow probe. It will be noted from FIG. 5A that with the trap valve maintained in the TRAP state, flow of the deuterated organic solvent DMSO-d6 is enabled from port 4 of the trap valve to port 5, and thus enabled to purge the microcoil NMR probe which is in fluid communication with port 5 of the trap valve. This flow of DMSO-d6 is typically sourced by a Harvard Instruments glass syringe perfusion pump, for the same reasons recited above for the $D_2O$ pump. The DMSO-d6 flow is typically of even lower flow rate, and lower total volume, than the above referenced $D_2O$ flow, which provides a long useable interval of operation between refills, even when modest syringe barrel sizes are employed. The bathing of the NMR probe with neat DMSO-d6 is useful from several standpoints. It generally ensures that any prior precipitates are removed from the flow conduits, and also prepares and prefills the entrance and exit conduits around the NMR flowcell with the same solvent as the analyte will be eluted in, to minimize magnetic susceptibility mismatch which can lead to poor (broad) NMR spectral line widths. Prior to DMSO-d6 edition, the trap bed is given a final purge with inert gas, followed by vacuum drydown, thus allowing the incoming DMSO-d6 solvent front to arrive in as sharp a configuration or front as possible, without mixing or blending on the leading edge with a preexisting $D_2O$ phase. Following this inert gas purge to waste, the trap valve is transitioned to the BACK ELUTE state, and flow from the DMSO-d6 syringe pump is enabled. This flow will be seen to back elute the trap (e.g., in the reverse direction from the trapping direction) into port 6 of the trap valve, and out via port 5 to the NMR microcoil probe. Back elation is useful for at least the following reason.

When trapping analyte with a very highly retentive phase, under proper trapping conditions, analyte will be retained at, or very close to, the extreme inlet end of the trap column. When that, region of the trap column bed becomes saturated with analyte, new incoming analyte will spill over into a subsequent region of the column bed, penetrating slightly further into the bed than the first portion of the analyte. As the trap bed slowly fills with retained analyte, this spillover will continue to occur, with successive sections of the bed becoming populated with analyte. In order to produce the narrowest and most intense analyte elution band, irrespective of the mass of analyte which is present, it is an advantage to back elate the bed with a very strongly solvating mobile phase. The back elution process will scavenge the spillover analyte as the strong solvent migrates through the bed, and will refocus the elution in a highly beneficial way. The swept up spillover will exit the column along with the preponderance of analyte trapped at the column head, thus maximizing the amount of analyte per unit volume of elating solvent. Given proper selection of trap column bed volume, this narrow, intense band back eluted from the trap column can have a volume at half height of only some 6 microliters. In contrast, that trapped analyte can have resided in the primary chromatography separation in a band of some 100 microliter volume, measured at half height. This significant reduction in the volume over which the sample mass is distributed, coupled with negligible (low or substantially no) loss of sample mass from the primary separation, is a statement of the impedance-matching which has been accomplished between the primary chromatography separation, and the microcoil NMR probe. The volume scales and concentration scales of the two processes (primary chromatography, and microcoil NMR detection) are very disparate, but are bridged efficiently by an appropriate impedance-matching mechanism, as described above. Appropriate impedance-matching is fundamental to achieving good utilization of sample mass, such that NMR spectra can be acquired with good S/N, while avoiding mass overloading of the primary chromatography separation, it will be further noted, with respect to FIG. 5A, that an inline capillary-scale UV absorbance detector can usefully be incorporated into the flow path leading from trap valve port 5 to the microcoil NMR probe. As shown below, such a detector can be used as an inline diagnostic tool to confirm the presence of analyte traversing the path to the NMR probe, prior to NMR spectroscopy being performed. Such capillary-scale UV absorbance detectors can be made small and relatively inexpensively, and the diagnostic utility which they can provide can be meaningful in practice.

Slicing of Multiple Peaks from a Chromatogram.

In a simple illustration of system operation, a single storage loon can be plumbed between an appropriate two ports of a single slicing valve. Such a configuration is capable of slicing a single component, or fraction, from a chromatographic separation, as illustrated and discussed above.

However, in various embodiments it can be desirable to slice more than one fraction from a given separation, and to maintain in isolation those respective slices for later processing such as trapping/refocusing, polishing, and spectroscopic analysis. The operation of an N-loop slicing apparatus for up to N fractions is nontrivial, if the intent is to produce shoes with substantially no carryover of sample or of extraneous chromatographic background from one fraction to the next. FIGS. 6A-D illustrate an embodiment of an N-loop slicing apparatus, which has been demonstrated to achieve or maintain the intended sample purity.

The valve in FIGS. 6A-D is the slicing valve which interlaces into the UHPLC chromatography stream (at the ports noted), and which asserts its slicing action as governed by in line detectors as discussed above. Rather than having a single external loop for sample capture, the slicing valve interfaces with two additional rotary selector valves (herein termed 1-of-N rotary selector valves), which operate as part of a hierarchical stream diversion architecture corresponding to a multiplex/demultiplex pair. Note that in practice, there is a length of connecting tubing enabling fluid communication between the slicing valve and the respective 1-of-N rotary selector valves. Appropriate management of the captive volume of liquid, within that connecting tubing is critical to proper system operation, and is discussed in farther detail below.

FIG. 6A illustrates an example "slice valve" shown in the state corresponding to chromatographic-stream sampling, in that the chromatographic stream is traversing the sampling loop of the valve. The loop expulsion flow is simply idling across the valve, without interacting with the sampling loop. The loop expulsion flow rate can be selected to be zero, or nonzero, in this state.

FIG. 6B illustrates an example "slice valve" shown in the state corresponding to no chromatographic stream sampling; rather, the loop expulsion flow is enabled to traverse the sampling loop, thereby causing sampled material contained within the sampling loop to be displaced out of the loop, toward the at-column dilution tee, and ultimately toward the trapping column.

FIG. 6C illustrates a pair of 1-of-N rotary selector valves (e.g., a multiplex/demultiplex pair) used to direct separate e.g., temporally and volumetrically-distinct) samplings of the chromatographic stream into respective loops, to support independent processing of those samplings without incurring cross-contamination of samples. The fluid port labeled "0", on each valve, is the common port, which is placed into fluid communication with one (and exclusively one) of the radially-disposed ports labeled "1" through "10", by action of the valve rotor. Alternating sample and bypass loops are populated around each valve, at the radially-disposed ports, such that incrementing of the selector valve rotor position achieves fluid communication with, alternately, a sample storage loop and a bypass loop. Bypassing allows for flushing of the valve passageways with loop expulsion solvent flow, at any time when chromatographic sampling is not occurring.

FIG. 6B illustrates an intercalation of the pair 1-of-N rotary selector valves from FIG. 6C into the fluid path of the "slice valve" of FIGS. 6A and 6B. Where the slice valve of FIGS. 6A and 6B implements just a single sampling loop, the arrangement of FIG. 6D allows the sampled chromatographic stream to be directed into a chosen 1 of 5 separate-and-distinct temporary-storage loops.

FIG. 6C depicts a larger and more detailed view of the pair of 1-of-N rotary selector valves. One can see that at odd numbered ports (e.g., at a pitch corresponding to every other port), a bypass functionality is implemented (see labels BP1, BP3, BP5, BP7, and BP9). At each even numbered port (thus also occurring at a pitch corresponding to every other port) is a sample containment loop (see labels SL2, SL4, SL6, SL8 and SL10).

In operation, referring to FIG. 6C, incoming liquid arrives at the central port of the left valve, labeled 0. In this example of a rotary shear seal valve, the valve controller actuates the valve rotor to bring about fluid communication between central port 0 and exclusively one of the radially disposed output ports numbered from 1-10. The valve internal architecture is of a break-before-make design, such that only a single central-to-radial flow path enabled at any given time, and that cross flow between adjacent ports is substantially eliminated. For the valve at the right in FIG. 6C, the flow direction is such that fluid arrives at a radially disposed port, numbered from 1-10, and departs that valve by way of the central port labeled 0. Again, the break-before-make internal design assures that only a single radial-to-central flow path is enabled at any given time, and that substantially no cross flow between radially disposed ports can occur.

Prior to the start of a chromatographic separation (e.g., as part of the run initialization for that separation), the slice valve and the pair of 1-of-N selector valves will be actuated so as to purge this section of the apparatus with either loop expulsion flow or chromatographic initial conditions flow (e.g., preceding any injection of sample into the chromatographic system). An important detail is that any analyte residual anywhere in the depicted valve structure be swept to waste so that it does not appear as a contaminant in any upcoming spectroscopy.

It will be seen that, based on the state of the slicing valve, either chromatography solvent or loop expulsion solvent can be used to purge or rinse the bypass loops and the sample collection loops of the multiplex/demultiplex pair, as well as the slice valve itself and the intervening tubing connecting the slice valve with the multiplex/demultiplex pair. Once this purge/rinse is accomplished, the slice valve is returned to non-slice or freely bypassing state, and the 1-of-N selector valves will be returned to position 1 (i.e., connecting radially disposed port 1 with the central/common port 0). Thus a bypass loop, BP1, is enabled for flow between the multiplex/demultiplex pair.

Slicing: At the start of the chromatographic run, an analyte or an analyte mixture is injected by the auto sampler, and begins to propagate through the separation column. When the chromatography system controller determines that a traction of interest has been detected, and following any programmed time delay, the slice valve is commanded to slice into the chromatographic separation stream. At this time, the separation stream will begin propagating through the slice valve and through the connecting tubing leading toward the 1-of-N selector valve shown at the left of FIG. 6C. Note however, that the selector valves are still dictating a bypass behavior. Liquid displaced into the inlet side of the 1 of N selector valve arrangement will cause non-sample laden or benign liquid (already resident within) to be purged from the downstream 1-of-N selector valve, at the right of FIG. 6C.

As the chromatographic flow rate is known to the chromatography system controller, and since the volume of the connecting tubing intervening between the slice valve and the first 1-of-N selector valve is known in advance (e.g., as part of the system hardware configuration), it is straightforward to make use of a time delay to cause the 1-of-N selector valves to advance to position 2 (i.e., a sample collection loop) when the sliced fraction is calculated to have arrived at port 0 of the upstream 1 of N selector valve. The two 1-of-N selectors operate in concert, changing position at the same time, to enable flow selectively through a defined bypass or a defined sample loop. In an illustrative embodiment, the selector valves increment then state or position (increment only; they do not retrace back to lower states/positions).

The calculated delay implemented as described above avoids capturing chromatographic baseline unrelated to the peak of interest. Chromatographic baseline will typically contain other materials from the separation unrelated to the analyte of interest, and thus comprising contaminants. A driving motivation in the instant invention is to produce analyte which is as free as possible from the presence of contaminants.

As the system controller detects that the last of the analyte of interest has passed the inline detector, and after application of any relevant time delay internal to the chromatography system, the slice valve is commanded to restore to the bypass or non-slicing state. Note that the tail of the analyte distribution will still reside in the intervening connecting tubing leading to the 1-of-N selector valve. If the tail were lost (e.g., diverted away), it would not contribute to the captured sample mass, and thus represent an undesired sample loss or wastage. However, the loop expulsion flow, which comprises a pure solvent with no analyte present, is now available to drive the tail of this analyte band forward into the inlet of the 1-of-N selector valve.

This loop expulsion flow, because it does not carry risk of introducing undesired analyte, can continue for a time increment which can be made generous (limited only by the need to avoid excessively displacing, and thus losing, the analyte already resident within the sample collection loop). After this increment of time (likewise under program control, and with prior knowledge of the loop expulsion flow rate), the 1-of-N selector valves are incremented to the next state or position, which is a Bypass state (BP3). In the bypass configuration, loop expulsion flow can proceed indefinitely without causing displacement of analyte resident in any collection loop.

Analyte Trapping and Polishing.

Figure 7A:
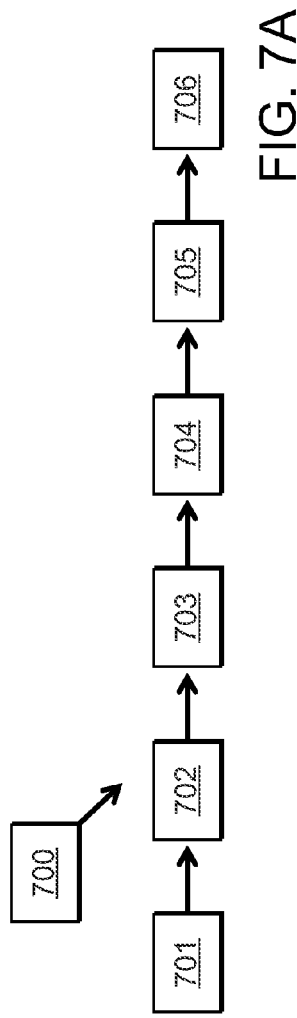
FIGS. 7A-D depict an example of trap operation in accordance with the invention.

The invention provides for methods (and corresponding apparatuses/systems) for analyte trapping and polishing 700 as depicted in FIG. 7A. In various embodiments, these methods include the steps of: (701) chromatographically separating a first fraction comprising a first analyte from a sample; (702) accumulating the first fraction in a sample collection loop; (703) trapping the first analyte on a stationary phase disposed within a trap defining a flow path through a first port to a second port and the stationary phase disposed therebetween; (704) flowing a scavenging gas, into the first port of the trap and concurrently achieving a vacuum at the second port, through the flow path, thereby drying the stationary phase; and (705) eluting the first analyte.

The step of chromatographically separating a first traction comprising a first analyte from a sample can be accomplished by various methods known in the art as well as the methods described herein.

The step of accumulating the first fraction in a sample collection loop can be accomplished by the methods described herein, e.g., as described in Example 1 and in connection with FIGS. 6A-D.

Figure 7B:
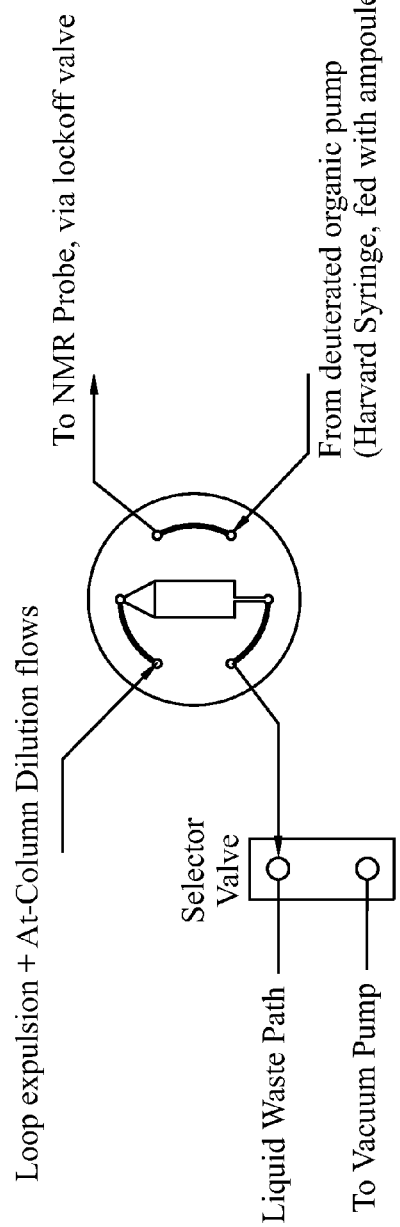

The step of trapping the first analyte on a stationary phase disposed within a trap defining a How path through a first port to a second port and the stationary phase disposed therebetween can be accomplished by the methods described herein, e.g., as depicted in FIG. 7B, which shows a trap valve in accordance with the invention, daring the sample trapping phase of operation (at column dilution employed).

In the example embodiment illustrated in FIG. 7B, the trap(ping) valve with associated trap(ping) column, depicting the valve state where sample trapping is enabled. Liquid waste from this trapping process is directed to a dedicated liquid waste path which is separate from the vacuum pump path, and is selectably enabled, in this valve state, a flow of deuterated organic solvent can idle toward and through the NMR flow cell, ensuring that the cell is purged of any prior contents, and well equilibrated to the solvent type used for analyte elution from the trap.

Figure 7C:
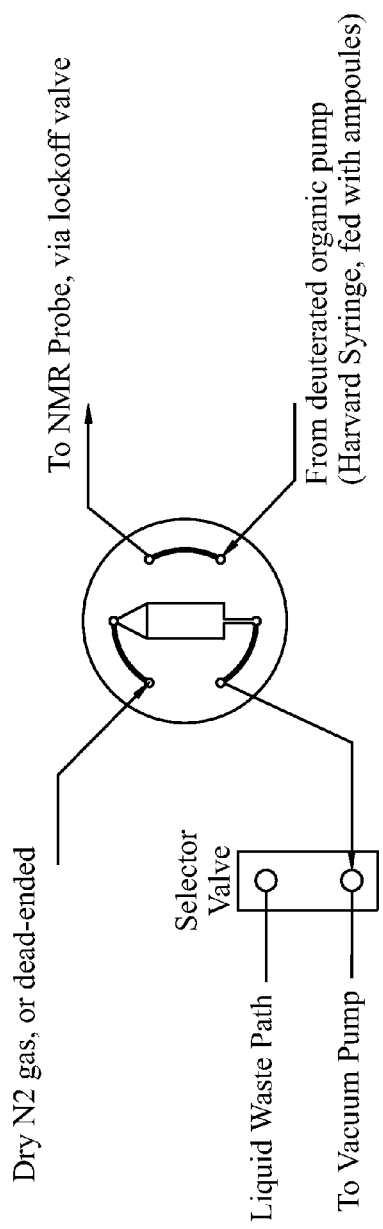

The step of flowing a scavenging gas, into the first port of the trap and concurrently achieving a vacuum at the second port, through the flow path, thereby drying the stationary phase can be accomplished by the methods described herein, e.g., as depicted in FIG. 7C, which shows a trap valve in accordance with the invention, during the sample polishing phase of operation.

In the example embodiment, illustrated in FIG. 7C, the trap(ping) valve with associated trap(ping) column, depicting the valve state where the final phase of sample polishing is accomplished. While retained analyte remains adsorbed to the trap column bed, the void volume of the trap column bed is purged of bulk liquid using compressed dry nitrogen (N2), and then the bed is pumped to a state of substantial dryness using the vacuum pump in conjunction with a scavenging flow of dry nitrogen. Note again that in this state of the trap valve, a flow of deuterated organic solvent can idle toward and through the NMR flow cell, ensuring that the cell is purged of any prior contents, and wed equilibrated to the solvent type used for analyte elution from the trap.

Figure 7D:
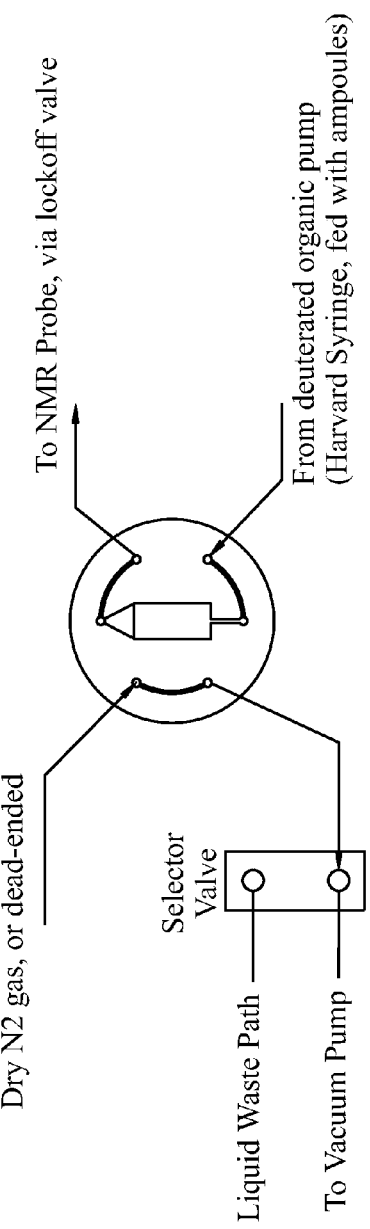

The step of eluting the first analyte can be accomplished by the methods described herein, e.g., as depicted in FIG. 7D, which shows a trap valve in accordance with the invention, during the back elution phase of operation.

In the example embodiment illustrated in FIG. 7D, the trap(ping) valve depicted in the back-elution state, where a flow of deuterated organic solvent traverses the trap bed and elutes the previously-trapped analyte, in a densely-concentrated band, toward the NMR flow cell. The vacuum pump is offline from the trap column at this stage of instrument operation, and can draw against a dead-ended connection, or against a restricted flow of dry nitrogen gas.

However, the methods need not include each of these steps. For example, in other embodiments, a method of chromatographic interfacing includes at least the steps of: (i) trapping an analyte from a chromatographically separated fraction of a sample onto a stationary phase disposed within a trap defining a flow path through the first port to a second port and a stationary phase disposed therebetween (e.g., as in 703); and (ii) flowing a scavenging gas, into a first port of the trap and concurrently achieving a vacuum at the second port, through the How path, thereby drying the stationary phase (e.g., as in 704).

In another embodiment, the steps of separating the at least one fraction and trapping the analyte further comprise the steps of: (1) detecting the presence of the analyte during primary chromatographic separation; (2) flowing the at least one fraction through a slice valve to a selector valve; (3) switching the selector valve from a bypass loop position to a collection loop position; (4) detecting at least one of the absence of the analyte and the presence of an undesired contaminant; and (5) switching the selector valve from the collection loop position to the bypass loop position.

In yet another embodiment, the method further includes: (i) chromatographically separating a second traction comprising a second analyte from the sample; (ii) accumulating the second fraction in a second sample collection loop; (iii) trapping the second analyte on the stationary phase of the trap after eluting the first analyte; (iv) flowing the scavenging gas, into the first port of the trap and concurrently achieving a vacuum at the second port, through the flow path, thereby drying the stationary phase; and (v) elating the second analyte.

In still another embodiment; (i) trapping the first analyte on the stationary phase disposed within a trap comprises flowing the first fraction from the first port to the second port and elating the first analyte comprises flowing an elating solvent from the second port to the first port; or (ii) trapping the first analyte on the stationary phase disposed within a trap comprises flowing the first fraction from the second port to the first port and elating the first analyte comprises flowing an eluting solvent from the first port to the second port.

In general the scavenging gas comprises dry nitrogen. For example, the dry nitrogen can be provided from a cryogenic system.

Flowing the scavenging gas can comprise a pulsatile introduction of scavenging gas. For example, the pulsatile introduction of scavenging gas comprises providing 'ON' pulses of about 100-200 milliseconds duration at a duty cycle of 1% or less.

Flowing the scavenging gas can comprise restricting the flow. For example, restricting the flow can comprise flowing the scavenging gas through a capillary restrictor. The scavenging gas can be flowed at a rate of about 0.0001 to 0.01 SCCM.

Drying the stationary phase can comprise eliminating substantially all solvent. This can be quantified, for example, by substantially achieving the base pressure of the vacuum source. For example, drying the stationary phase comprises achieving a vacuum having a pressure of less than about 15 mTorr.

In various embodiments, the trapping step further comprises flowing a weak solvent comprising at least one of a protonated or deuterated solvent through the flow path. The method can further comprise eluting the analyte using DMSO-d6. Examples are discussed in further detail below.

After elation, the method can further comprise analyzing the analyte of interest by spectrometry, a chemical assay, or a bioassay (e.g., as in optional step 706).

Figure 8:
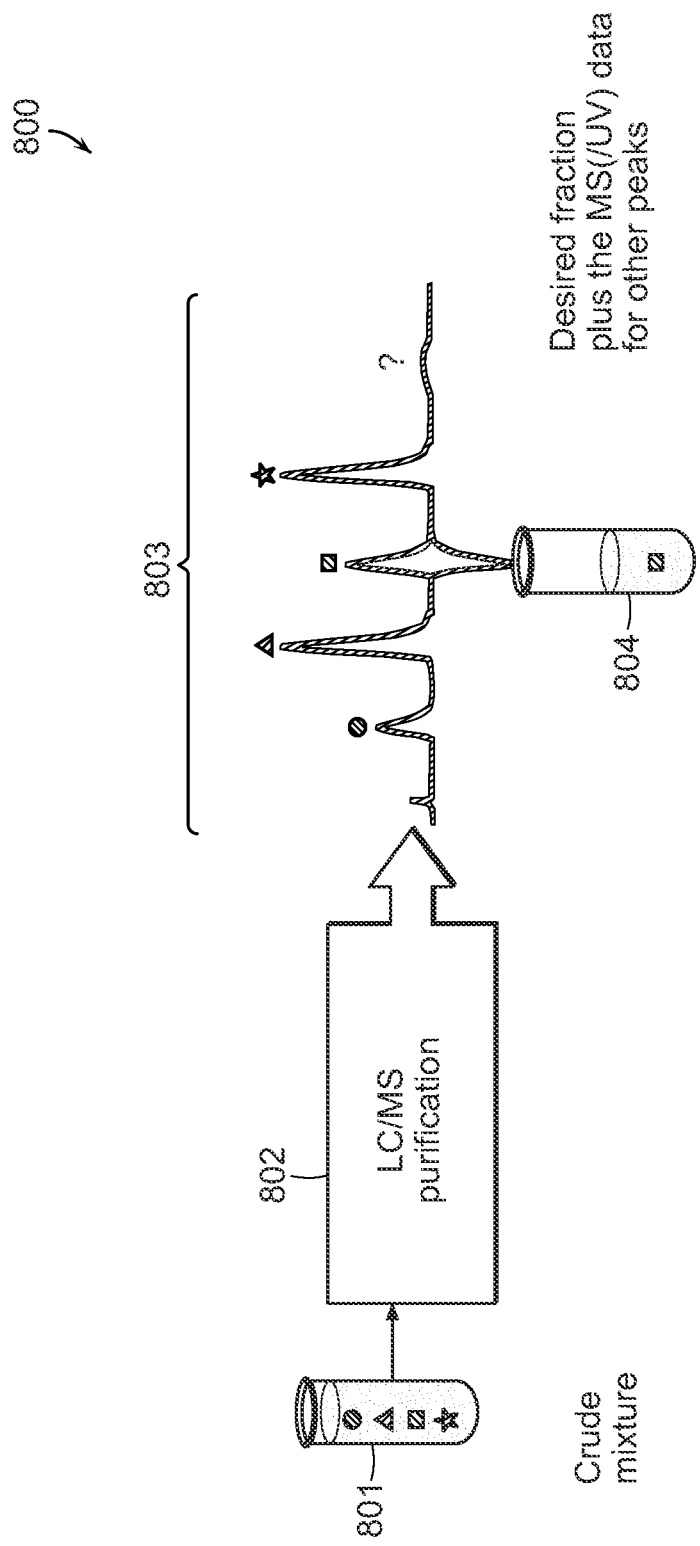
FIG. 8 depicts a generic method for mass directed autopurification.

FIG. 8 shows a generic method for mass directed autopurification 800 (in this case, implemented on a Waters Technologies Corporation FractionLynx™ Application Manager) where a crude mixture 801 is separated or fractionated 802 into components 803, with a single one of those components 804 being selected for capture on the basis of mass spectral data (e.g., m/z ratio), UV absorbance data, time (e.g., retention time), or data arising from another detector type. Mass directed autopurification software can be advantageously applied in implementing the present invention (e.g., by managing the chromatographic interfacing apparatus).

Figure 9A:
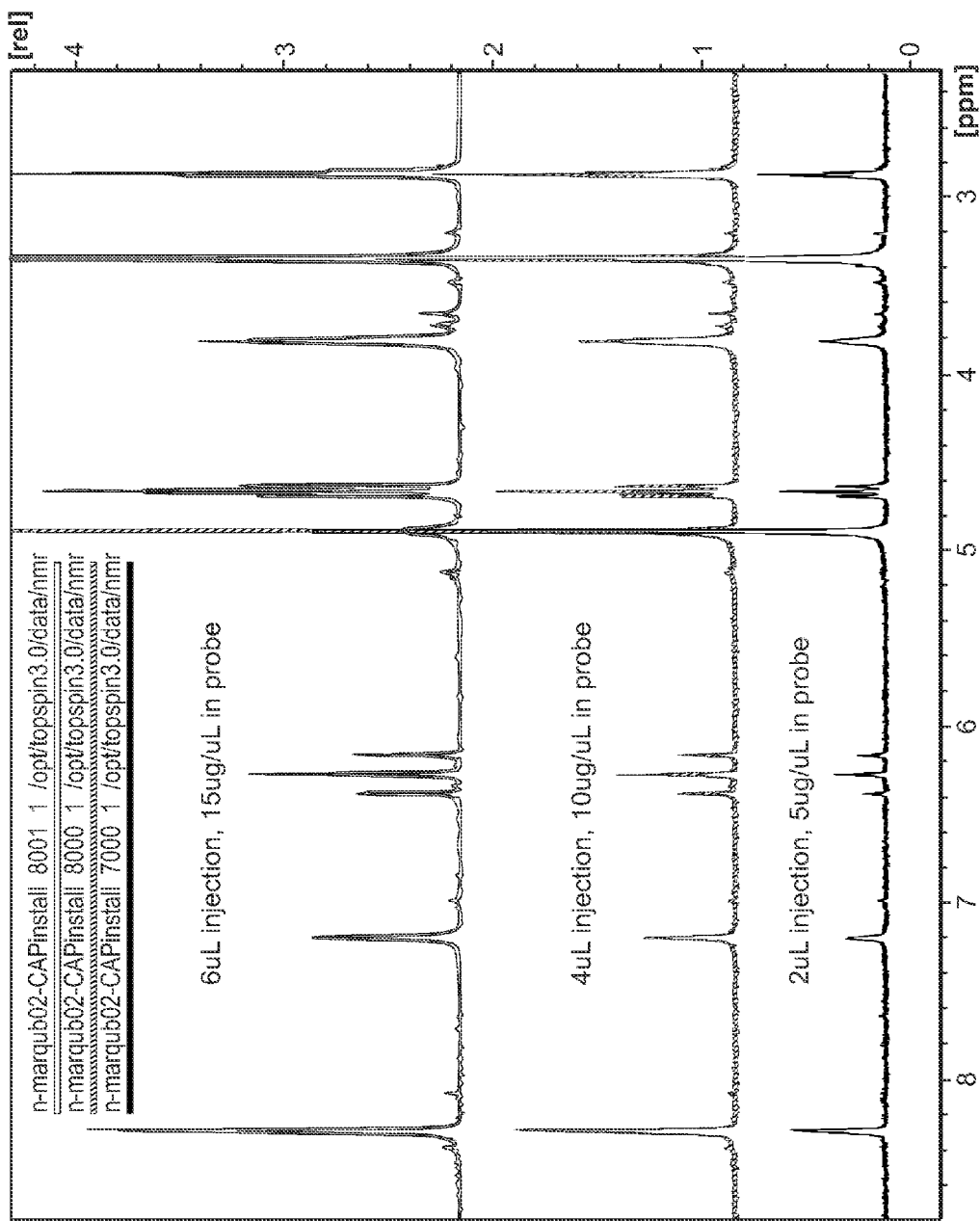
FIGS. 9A and B depict NMR spectra for cis and trans isomers of green tea catechins.

FIG. 9A shows one advantageous application of the present invention with the successful aggregation of sample, in increasing amounts, at the trap column, in response to increasing sample mass being injected onto the primary chromatographic column. S/N ratio in the NMR spectrum is increasing as trapped sample mass increases ("2 uL injection, 5 ug/uL in probe"→"4 uL injection, 10 ug/uL in probe"→"6 uL injection, 15 ug/uL in probe").

Figure 9B:
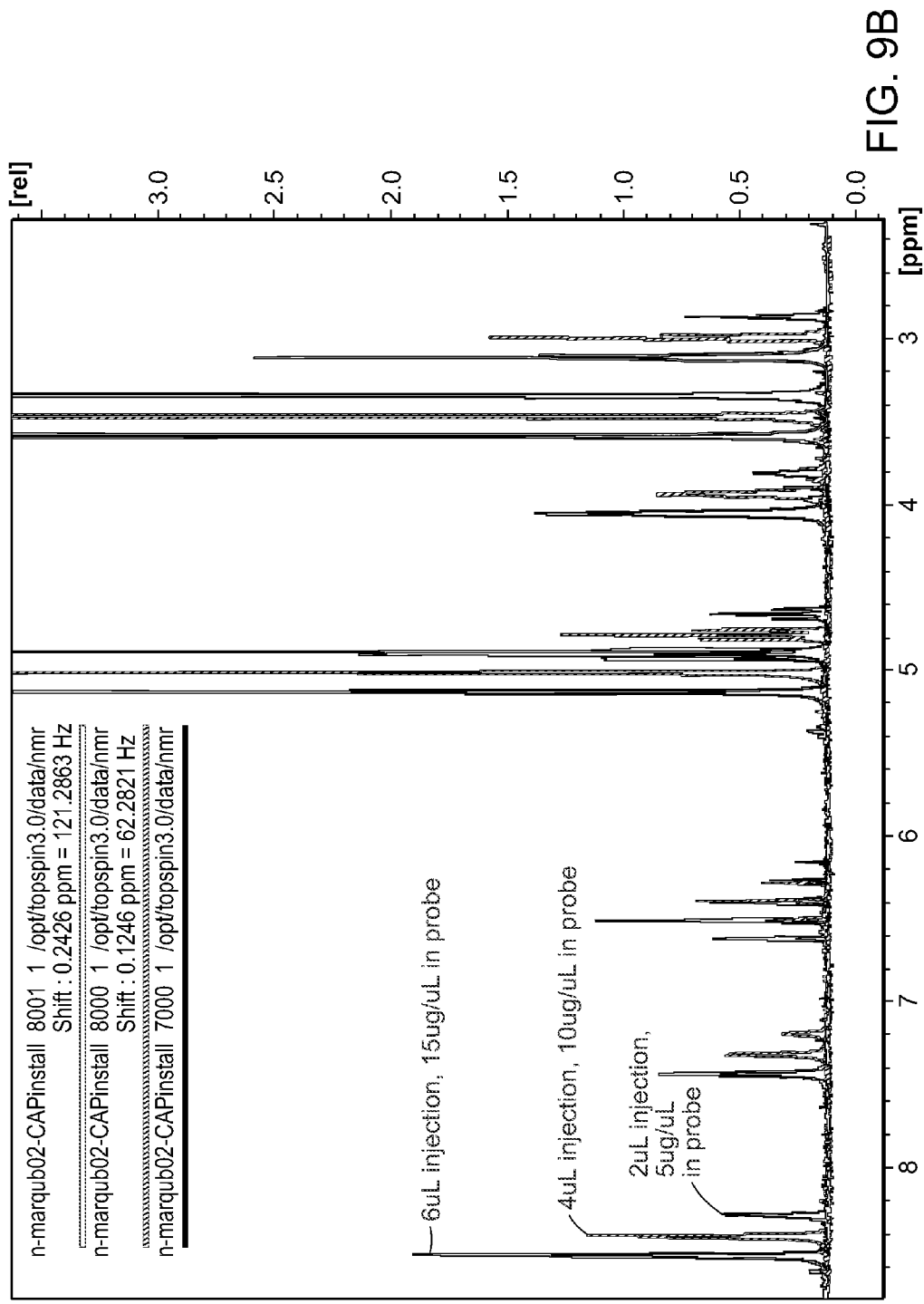

FIG. 9B shows an overlay, bar comparison purposes, of the data from FIG. 9A. A sense for the linearity of the system is obtained from this view.

Figure 10:
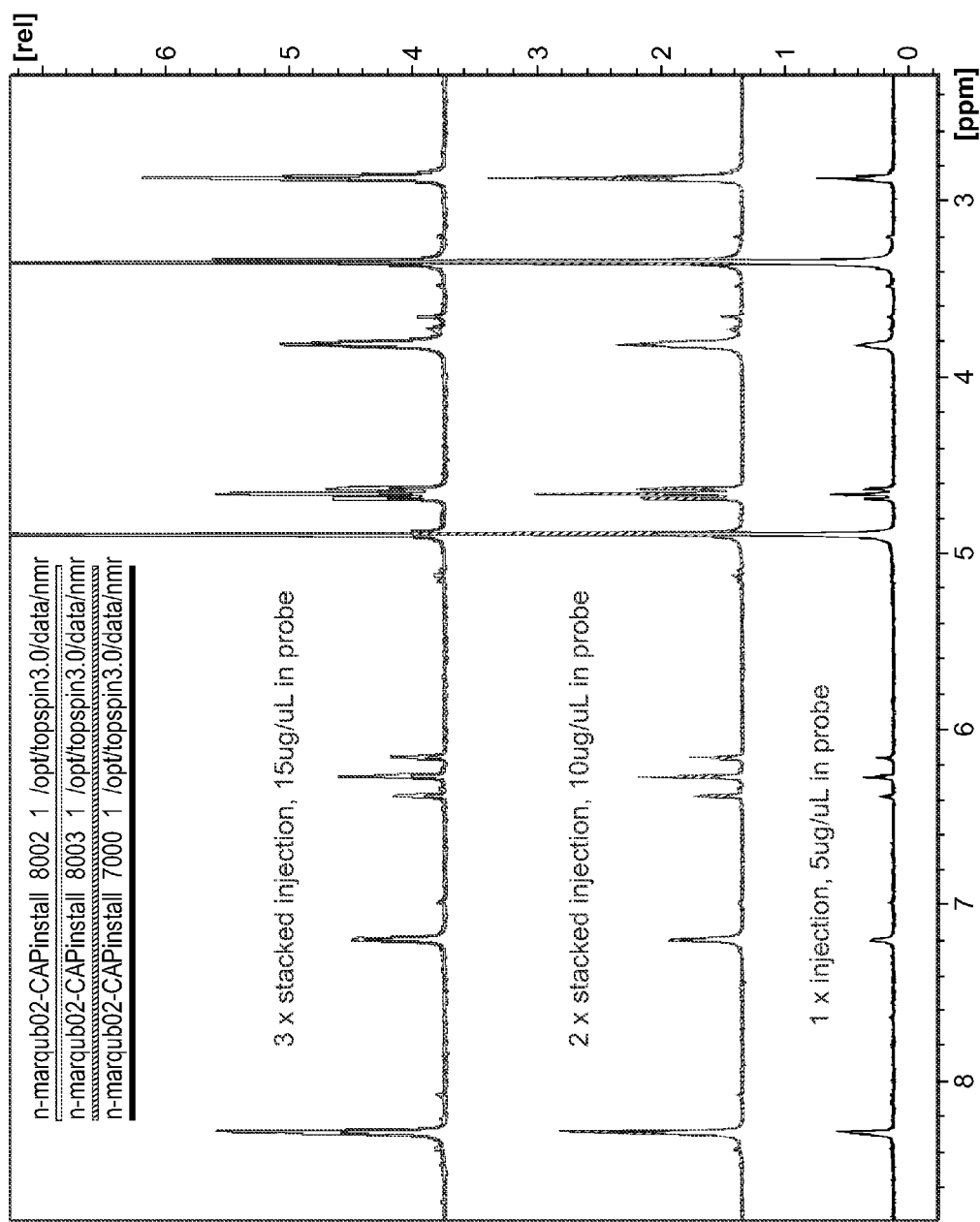
FIG. 10 depicts structures and m/z values for cis and trans isomers of green tea catechins.

FIG. 10 shows an increasing signal, and S/N ratio, obtained by aggregating sample from multiple/sequential chromatographic separations (i.e., "stacking" of sample injections). Analyte sliced from sequential primary chromatography separations is aggregated at the trap column. The data of FIG. 10 demonstrates the additivity and/or linearity of the aggregation method.

Generalization of the Interface Technique Beyond NMR Applications.

The ability to slice a carefully delineated fraction from a UHPLC separation, and to subsequently migrate that slice to a trapping column or bed where analyte re focusing is accomplished, coupled with an ability to elute that refocused analyte in substantially a single, densely concentrated band or impulse, is a useful interfacing technique in general. Applications which come readily to mind axe the interfacing of a first stage of chromatographic separation (in this example or illustrative embodiment, reversed phase UHPLC) with a second stage of chromatographic separation (non-limiting examples being: normal phase liquid chromatography, and supercritical fluid chromatography ("SFC"), or carbon dioxide-based chromatography).

Given the analyte refocusing which is achievable, as well as the conservation of sample (minimized sample loss, as the sample is not removed from the fluid conduit system into vials, etc., where such losses typically occur), it is plausible to envision the linking or chaining of more than two separation processes using the above technique. As a practical matter, some laboratories may wish to purify (by means of a UHPLC separation) small amounts of a critical sample, and then collect that sample for use in an entirely different assay occurring elsewhere within the business, such as a bioassay, and in such a circumstance, the above referenced apparatus and method could be employed to fractionate, concentrate, and collect with high efficiency, a small analyte amount into a receptacle of choice, such as a microtiter plate or vial.

One can see that the microcoil NMR flowcell examples discussed herein are one specialized instance of a receiving device, and that any number of different choices exist for a receiving device. Indeed, a low volume NMR tube, such as the 1.7 mm diameter class of such devices, termed capillary tubes, might be the receiving device chosen for particular applications, for interfacing a chromatography separation with NMR spectroscopy.

Mitigation of Protonated and/or Deuterated Solvent Interference.

As discussed above, it is important to substantially eliminate proton NMR signal arising from solvent protons, as solvent protons are numerically far more abundant (e.g., normally present at concentrations several orders of magnitude higher than the concentration of analyte protons). It is the analyte protons which produce the signal of interest in proton-NMR spectroscopic analysis, and one seeks to avoid a situation where the signal of interest is dwarfed by a background signal. When such background signals are of very high magnitude, they can saturate the RF receiver circuitry, compromising or even precluding detection of the analyte signals.

Furthermore, for analyte residing within the interrogated region of the microcoil flow probe, the homogeneity of the magnetic field bathing that analyte is critical to achieving appropriate and useful spectroscopic line width in the NMR analysis. It is commonly accepted that part per billion field homogeneity is a requirement, and the achievement of such extreme field homogeneity requires, in turn, that discontinuities or disruptions in the magnetic environment within, or surrounding, the interrogated region of the flow probe, be reduced to an absolute minimum.

Use of $D_2O$ to equilibrate away solvent protons from the trap retained analyte is indeed effective at accomplishing that specific task, but leaves behind $D_2O$ molecules which can become solvated by the trap elution solvent and migrated downstream along with the analyte. The capillary conduits leading to and from the microcoil flowcell are prefilled with neat organic solvent (the elution solvent), whereas the analyte departs the trap column and migrates to the microcoil flowcell in a liquid environment which is a mixture of $D_2O$ and elution solvent.

One could think of this fluid microenvironment bracketing the analyte as being a very low volume compositional gradient regime. Mixtures of $D_2O$ and an organic solvent such as MeOH-d4 or DMSO-d6 have different magnetic susceptibilities than the neat or pure organic solvents, and thus the presence of this gradient regime, bracketing the analyte, produces inhomogeneity in the magnetic environment bracketing the flowcell at the time of analysis. This type of magnetic perturbation is to be avoided, as it leads to excessively broad NMR line widths which are not useful for spectroscopic analysis.

Similarly, gas drying steps achieved with compressed gas will leave the trap bed filled with gas, and upon trap elution with the organic solvent, will cause a gas bubble to be displaced and migrated toward and through the microcoil flowcell. As with the $D_2O$ situation discussed above, the parking of the analyte in the microcoil flowcell for NMR analysis results in the gas bubble becoming parked in a position typically just beyond the fluid exit of the flowcell. Once again, this results in a magnetic inhomogeneity proximal to, and therefore asserting influence on, the interrogated region of the flowcell, with concomitant negative effect on the quality of the spectroscopy.

In various embodiments, the present invention provides solutions to these problems through washing of trap retained analyte with a deuterated or deuterium substituted phase such as deuterium oxide ($D_2O$), followed by, or interspersed with, dry nitrogen gas expulsion steps, which equilibrates away essentially all of the accessible protonated solvent, while leaving the analyte immobilized on the trapping column stationary phase.

In various embodiments, the invention employs a high quality vacuum to: (1) dry the trap of $H_2O$, $D_2O$, or other deuterated washing solvent, and (2) to eliminate the situation where a gas bubble is displaced downstream along with the analyte, upon trap elution. An example system configuration was produced which included a dry type roughing pump (e.g., Alcatel Model ACP40 dry pump) disposed at the trap valve to operate cooperatively with a valved introduction of dry nitrogen. The dry pump was routinely capable of producing pressures of less than 15 mTorr, and tints causing substantially complete drying of the stationary phase. In one embodiment, this drying was expedited by allowing a very low flow of rarefied dry nitrogen to percolate through and thus scavenge the bed, while vacuum pumping was applied to the opposing end of the bed.

Two different types of gas flow control techniques are: (1) a pulsed introduction of compressed dry nitrogen, where the ON pulse was of extremely low temporal width and duty cycle; and (2) a capillary restrictor limited flow of dry nitrogen from a pressurized source. Because the capillary restrictor limited the incoming gas flow rate, and because the vacuum pump was pulling or pumping continuously at the outlet side, the column bed was exposed to a vacuum condition which included a very low flow of scavenging gas. Because the trap bed, by definition, is an exceedingly labyrinthine structure with very small lineal dimensions of void spaces or channels, a scavenging gas flow was considered to be important in migrating evaporated solvent molecules through, and out of, this bed.

Drying as an Alternative to Liquid Phase Equilibration Processes for Elimination of Protonated Solvents.

As discussed above, perfusing a trap column bed with a deuterated phase of weak solvating strength (e.g., $D_2O$) can be utilized to: (a) leave the analyte compound retained/immobilized on the trap bed, and (b) to equilibrate away protonated weak solvent residual in bed following the sample trapping phase of system operation. Such equilibration arises from the deuterated phase intermingling with, solvating, and transporting downstream, a like, non-deuterated phase (e.g., $D_2O$ equilibrating away $H_2O$, for the case of a reversed phase trapping process). Such a liquid phase equilibration process, earned to completion, will leave the trap bed with a concentration of residual protons (i.e., residual protonation) which will be reflective of the quality of the incoming deuterated phase (Commercially, a deuterated phase such as $D_2O$ is practically available at qualities of part per thousand residual protonation).

Lower or higher residual protonation levels are typically available at higher or lower purchase price, respectively.) However, as discussed above, one is then confronted with eliminating the $D_2O$ from the bed, as its presence intermixed with the analyte in the elution band was shown to be disruptive to microcoil NMR spectroscopy. It becomes apparent that an $H_2O$ to $D_2O$ substitution step is extraneous if the overall procedure still requires elimination of $D_2O$ Effort was then expended to evaluate direct elimination (by dry down) of $H_2O$ in the absence of a $H_2O$ to $D_2O$ substitution. If anything, vapor pressure considerations should favor more rapid drydown of $H_2O$ versus $D_2O$. We learned that direct drydown of $H_2O$ was indeed a time-effective procedure, and was capable of producing dryness of the trap stationary phase consistent with excellent NMR spectroscopy results. Both the NMR line shape/line width and the water proton peak height/peak area, were well within acceptable limits for high quality NMR spectroscopy.

As proton NMR spectroscopy comprises an extremely sensitive water detector, it follows that analyte polishing via this technique is producing a very high quality of result, whether the intended next analytical step is NMR spectroscopy, or some other analytical process which can be sensitive to the presence of liquid solvents or gases residual from the immediate prior chromatography separation.

FIG. 11A illustrates a proton-NMR spectrum of the analyte Flavone, obtained after 7.5 hours of trap bed dryout using a flow of compressed dry nitrogen as the sole drying method. While the spectral quality obtained is good, the 7.5 hour drying time is a burdensome time-penalty on the analysis.

Figure 11B:
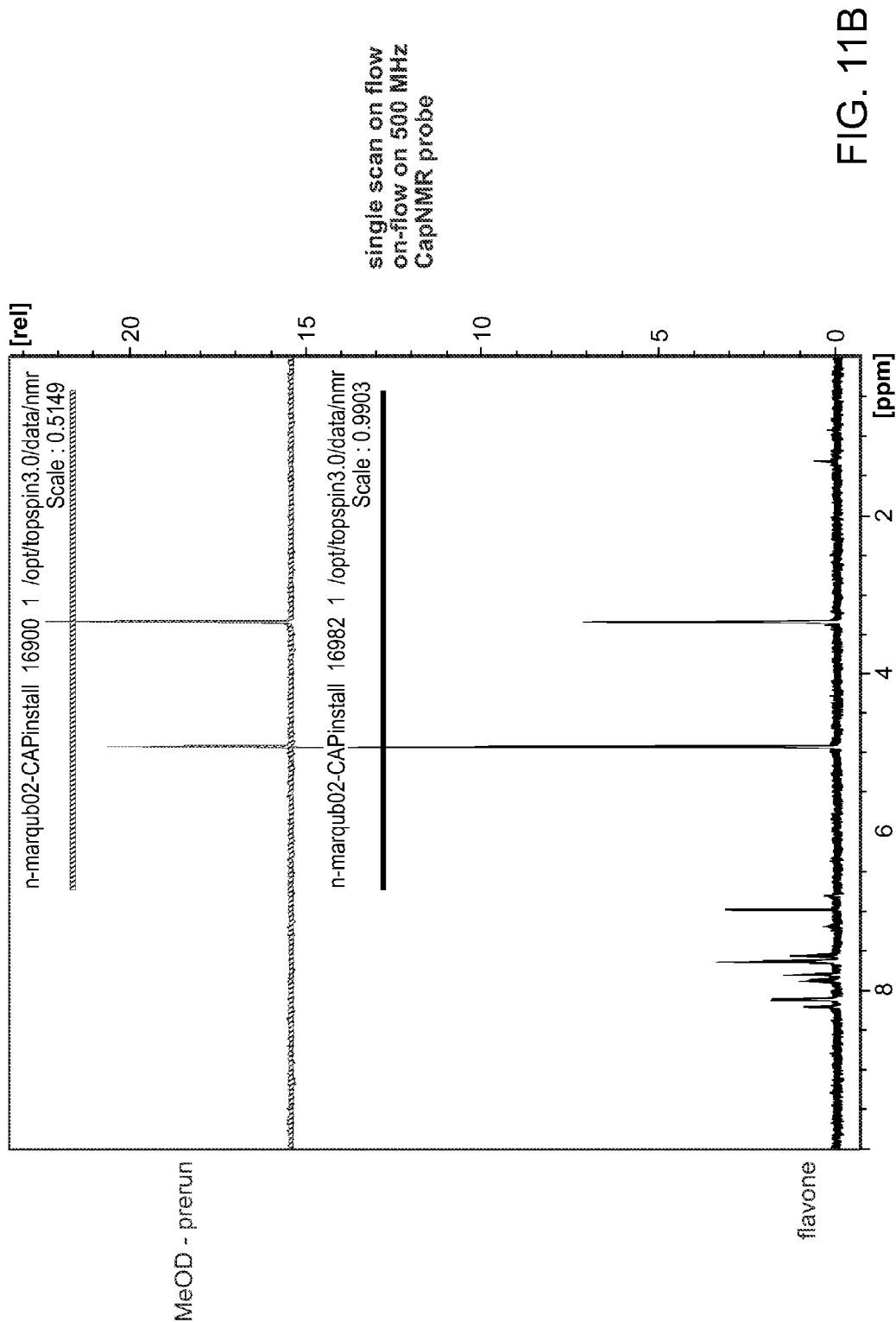
FIGS. 11A and B depict experimental results from an exemplary implementation of the present invention.

FIG. 11B illustrates a proton-NMR spectrum of the analyte Flavone, obtained after 30 minutes of trap bed dryout using a restricted flow (e.g., implemented using a capillary restrictor in accordance with the present invention) of dry nitrogen in conjunction with vacuum pumping. The nitrogen traversing the trap bed is employed as a scavenging gas, and is in a highly rarefied form in response to the prevailing vacuum conditions. Highly satisfactory drying was demonstrated using only 6.6% of the drying time employed for FIG. 11A, and even shorter times are possible. It is important to note that 30 minutes is not a limiting value—both shorter and longer are encompassed by various embodiments of the present invention.

Use of DMSO-d6 as an Elation Solvent.

Dimethyl sulfoxide (DMSO) in either its deuterated form (i.e., DMSO-d6) or its undeuterated or protonated form (i.e., DMSO), is not customarily considered an elation solvent for chromatography. Its viscosity is relatively high (1.996 cP at 20° C.), and it lacks the transparency in the deep UV part of the electromagnetic spectrum, which would otherwise allow for common UV absorbance detector types to be utilized for analyte detection. As a laboratory solvent, it is capable of dissolving polar and nonpolar compounds, and is miscible with water and with a useful range of organic solvents. It is considered a universal solvent in the small molecule pharmaceutical realm.

In the interfacing method described above, the trap column comprises a relatively short bed which need not be packed with extremely small diameter particles. To the contrary, in an illustrative embodiment, the trap is packed with relatively large diameter particles in the approximate size range of 15 to 25 micrometers diameter. When NMR detection is employed, the UV spectral cutoff behavior of DMSO is substantially of no consequence, as the spectroscopy being performed is of a completely separate and distinct type from UV absorbance, being based on mechanisms unrelated to UV absorbance.

Applications in LC-SCD.

X-Ray Single Crystal Diffraction (SCD) is a known crystallographic technique where the molecular structure of an analyte compound which has been isolated/purified and crystallized is inferred from the X-Ray diffraction pattern resulting from X-irradiation of the highly-ordered crystal, interpretation of the diffraction pattern may be accomplished by software such as that available under license from the Gottingen University Department of Structural Chemistry, and known as "SHELX" Conventional SCD requires the presence of sufficient compound to produce a crystal of the necessary size for analysis, and it requires a compound which is amenable to crystallization. In practice, the crystallization of unknowns may be time-consuming and labor-intensive, and may not, in the end, result in formation of a crystal suitable for crystallographic analysis.

A modern variant of SCD reported recently by Inokuma et al., 2013, "X-Ray Analysis on the Nanogram to Microgram Scale Using Porous Complexes," (Nature 495, 461-466), overcomes several of the limitations of SCD as practiced earlier. The authors describe a new method involving synthesis of a porous-metal complex loosely referred-to as a crystalline sponge. This backbone network is itself a highly-ordered structure. Into the void spaces of this sponge, a solvated analyte is allowed to penetrate, where it takes up residence in a highly-ordered and oriented manner due to coordination and complexation produced with respect to the metal backbone. In this way, X-Ray diffraction studies can be carried out without the a priori need to generate crystals of the unknown analyte. The analyte mass required for structural analysis is very much reduced, and may be generally on the nanogram to low-microgram range.

Thus the analyte need not be handled as a crystal at any point. Rather, it needs to be highly purified, and delivered to the porous metal complex in a solvent of choice (i.e., as a solvated species). These requirements are consistent with the capabilities of the instant invention.

In the application of porous-complex SCD to analytes prepared through use of the chromatographic interfacing methods and/or apparatuses of the invention (e.g., as opposed to flow NMR), the trap elution can be directed, not to a microcoil flowcell, but rather to a low-volume total-recovery vial or similar receptacle, in which the porous metal complex is present, awaiting the wicking-up of the analyte for analysis by SCD.

What is claimed is:

1. An apparatus for chromatographic interfacing comprising:
   an interfacing unit including
      (i) a chromatographic inflow valve positioned to receive a chromatographic sample separation flow,
      (ii) a chromatographic outflow valve that allows discharge of the sample separation flow,
      (iii) a loop expulsion inflow valve positioned to receive an expulsion fluid flow, and
      (iv) a loop expulsion outflow valve in fluid communication with the loop expulsion inflow valve and that allows discharge of a fluid;
   a sample acquisition unit including
      (i) an inflow selector in selectable fluid communication with the chromatographic inflow valve or the loop expulsion inlet valve,
      (ii) an outflow selector in fluid communication with the loop expulsion outflow valve, and
      (iii) one or more collection loops, each loop being independently selectable to establish fluid communication between the inflow selector valve and the outflow selector valve; and
   a sample trapping unit including
      (i) a trap in selectable fluid communication with the loop expulsion outflow valve and defining a flow path from a first port to a second port and through a stationary phase disposed therebetween, the stationary phase allows for trapping of an analyte of interest from a fraction of the chromatographic sample separation flow, and
      (ii) a scavenging gas source in selectable fluid communication with the flow path and a vacuum source in selectable fluid communication with the flow path, the scavenging gas source and vacuum source to substantially dry the stationary phase.

2. The apparatus of claim 1, wherein the sample acquisition unit further includes one or more bypass loops, each bypass loop being independently selectable to establish fluid communication between the inflow selector valve and the outflow selector valve.

3. The apparatus of claim 1, wherein the sample acquisition unit further includes two or more collection loops and two or more bypass loops, each loop being independently selectable to establish fluid communication between the inflow selector valve and the outflow selector valve.

4. The apparatus of claim 1, further comprising a chromatograph providing the flow from the chromatographic separation of the sample.

5. The apparatus of claim 4, wherein the chromatograph comprises a liquid chromatograph or a supercritical fluid chromatograph.

6. The apparatus of claim 1, wherein the inflow selector comprises a slice valve.

7. The apparatus of claim 1, wherein the inflow selector and outflow selector comprise a rotary selector valve for establishing fluid communication between a predetermined collection loop or bypass loop.

8. The apparatus of claim 7, wherein the rotary selector valve comprises a break before make design.

9. The apparatus of claim 1, wherein drying the stationary phase comprises eliminating substantially all solvent.

10. The apparatus of claim 9, wherein the solvent comprises a protonated or deuterated solvent.

11. The apparatus of claim 1, wherein the scavenging gas comprises dry $N_2$ gas.

12. The apparatus of claim 1, wherein the scavenging gas source provides a pulsed introduction of compressed $N_2$ gas.

13. The apparatus of claim 1, wherein the scavenging gas source further comprises a restrictor that controls pressure at the first port of the trapping column.

14. The apparatus of claim 1, wherein the vacuum source comprises a dry pump, or an oil sealed pump having a filter that removes volatilized oil from the oil sealed pump.

15. The apparatus of claim 1, further comprising a vacuum source controller that determines when the trap is dry.

16. The apparatus of claim 1, further comprising an analyte detector and a controller that determines when the analyte of interest is present in the chromatographic stream and to control the inlet selector accordingly.

17. The apparatus of claim 1, further comprising an eluting solvent source.

18. The apparatus of claim 1, further comprising a spectrometer for analyzing the analyte of interest.

19. The apparatus of claim 1, further comprising a chemical or bioassay for analyzing the analyte of interest.

20. The apparatus of claim 1, further comprising a time delay controller that adjusts for dead volume.

21. A method of chromatographic interfacing comprising the steps of:
   trapping an analyte from a chromatographically separated fraction of a sample onto a stationary phase disposed within a trap defining a flow path through the first port to a second port and a stationary phase disposed therebetween; and
   flowing a scavenging gas, into a first port of the trap and concurrently achieving a vacuum at the second port, through the flow path, thereby drying the stationary phase.

22. A method of chromatographic interfacing comprising the steps of:
   chromatographically separating a first fraction comprising a first analyte from a sample;
   accumulating the first fraction in a sample collection loop;
   trapping the first analyte on a stationary phase disposed within a trap defining a flow path through a first port to a second port and the stationary phase disposed therebetween;
   flowing a scavenging gas, into the first port of the trap and concurrently achieving a vacuum at the second port, through the flow path, thereby drying the stationary phase; and
   eluting the first analyte.

23. The method of claim 22, wherein scavenging gas comprises dry nitrogen.

24. The method of claim 23, wherein the dry nitrogen is provided from a cryogenic system.

25. The method of claim 22, wherein flowing the scavenging gas comprises a pulsatite introduction of scavenging gas.

26. The method of claim 25, wherein the pulsatite introduction of scavenging gas comprises providing on pulses of about 100-200 milliseconds duration at a duty cycle of 1% or less.

27. The method of claim 22, wherein flowing the scavenging gas comprises restricting the flow.

28. The method of claim 27, wherein restricting the flow comprises flowing the scavenging gas through a capillary restrictor.

29. The method of claim 22, wherein the scavenging gas is flowed at a rate of about 0.0001 to 0.01 SCCM.

30. The method of claim 22, wherein drying the stationary phase comprises achieving a vacuum having a pressure of less than about 5 mTorr.

31. The method of claim 22, wherein drying the stationary phase comprises eliminating substantially all solvent.

32. The method of claim 22, wherein drying the stationary phase comprises substantially achieving the base pressure of the vacuum source.

33. The method of claim 22, wherein the trapping step further comprises flowing a weak solvent comprising at least one of a protonated or deuterated solvent through the flow path.

34. The method of claim 22, further comprising eluting the analyte using DMSO-d6.

35. The method of claim 22, further comprising analyzing the analyte of interest by spectrometry, a chemical assay, or a bioassay.

36. The method of claim 22, wherein the chromatography comprises liquid chromatography or supercritical fluid chromatography.

37. The method of claim 22, wherein the steps of separating the at least one fraction and trapping the analyte further comprise the steps of:
   (1) detecting the presence of the analyte during primary chromatographic separation;
   (2) flowing the at least one fraction through a slice valve to a selector valve;
   (3) switching the selector valve from a bypass loop position to a collection loop position;
   (4) detecting at least one of the absence of the analyte and the presence of an undesired contaminant; and
   (5) switching the selector valve from the collection loop position to the bypass loop position.

38. The method of claim 22, further comprising
   chromatographically separating a second fraction comprising a second analyte from the sample;
   accumulating the second fraction in a second sample collection loop;
   trapping the second analyte on the stationary phase of the trap after eluting the first analyte;
   flowing the scavenging gas, into the first port of the trap and concurrently achieving a vacuum at the second port, through the flow path, thereby drying the stationary phase; and
   eluting the second analyte.

39. The method of claim 22, wherein
   trapping the first analyte on the stationary phase disposed within a trap comprises flowing the first fraction from the first port to the second port and eluting the first analyte comprises flowing an eluting solvent from the second port to the first port; or
   trapping the first analyte on the stationary phase disposed within a trap comprises flowing the first fraction from the second port to the first port and eluting the first analyte comprises flowing an eluting solvent from the first port to the second port.

* * * * *